(12) United States Patent
Aboul-Hosn et al.

(10) Patent No.: US 7,731,675 B2
(45) Date of Patent: Jun. 8, 2010

(54) GUIDABLE INTRAVASCULAR BLOOD PUMP AND RELATED METHODS

(75) Inventors: Walid N Aboul-Hosn, Fair Oaks, CA (US); William R Kanz, Sacramento, CA (US); Bruce A. Baker, Placerville, CA (US)

(73) Assignee: Maquet Cardiovascular LLC, San Jose, CA (US)

( * ) Notice: Subject to any disclaimer, the term of this patent is extended or adjusted under 35 U.S.C. 154(b) by 28 days.

(21) Appl. No.: 11/375,926

(22) Filed: Mar. 15, 2006

(65) Prior Publication Data
US 2006/0161095 A1 Jul. 20, 2006

Related U.S. Application Data

(62) Division of application No. 10/070,178, filed as application No. PCT/US00/24515 on Sep. 1, 2000, now Pat. No. 7,022,100.

(60) Provisional application No. 60/152,249, filed on Sep. 3, 1999.

(51) Int. Cl.
*A61M 37/00* (2006.01)
*A61M 5/00* (2006.01)
*A61M 1/10* (2006.01)
*A61N 1/362* (2006.01)

(52) U.S. Cl. .................... 604/6.11; 604/6.16; 604/8; 600/16; 623/3.1; 415/900

(58) Field of Classification Search .............. 600/16, 600/18; 604/7, 8, 9, 6.11; 623/3.1, 3.13, 623/3.26–3.28, 3.3; 415/900
See application file for complete search history.

(56) References Cited

U.S. PATENT DOCUMENTS

| | | | |
|---|---|---|---|
| 3,585,983 A | | 6/1971 | Kantrowitz et al. |
| 3,602,009 A | * | 8/1971 | Powell ................... 464/52 |
| 3,904,901 A | | 9/1975 | Renard et al. |
| 4,391,547 A | * | 7/1983 | Jackson et al. ........... 403/341 |
| 4,392,836 A | * | 7/1983 | Sugawara ................ 464/52 |
| 4,413,989 A | * | 11/1983 | Schjeldahl et al. ..... 604/103.13 |
| 4,591,355 A | * | 5/1986 | Hilse .................... 604/159 |
| 4,625,712 A | * | 12/1986 | Wampler ................ 600/16 |
| 4,696,667 A | * | 9/1987 | Masch ................... 604/22 |

(Continued)

FOREIGN PATENT DOCUMENTS

CA    2 256 427    10/2009

(Continued)

OTHER PUBLICATIONS

Online encyclopedia article "Pyrolytic Carbon" accessed Feb. 19, 2009. http://en.wikipedia.org/wiki/Pyrolytic_carbon.*

(Continued)

*Primary Examiner*—Leslie R. Deak
*Assistant Examiner*—Adam Marcetich
(74) *Attorney, Agent, or Firm*—Law Office of Alan W. Cannon

(57) ABSTRACT

An improved intravascular blood pump and related methods involving the broad inventive concept of equipping the intravascular blood pump with guiding features such that the intravascular blood pump can be selectively positioned at a predetermined location within the circulatory system of a patient.

11 Claims, 18 Drawing Sheets

U.S. PATENT DOCUMENTS

| | | | |
|---|---|---|---|
| 4,704,121 A | | 11/1987 | Moise |
| 4,728,319 A | * | 3/1988 | Masch .................. 604/22 |
| 4,817,586 A | | 4/1989 | Wampler |
| 4,895,557 A | | 1/1990 | Moise et al. |
| 4,908,012 A | * | 3/1990 | Moise et al. ............. 600/16 |
| 4,909,781 A | * | 3/1990 | Husted .................. 604/22 |
| 4,917,102 A | * | 4/1990 | Miller et al. ............ 600/585 |
| 4,919,647 A | * | 4/1990 | Nash .................... 600/16 |
| 4,955,856 A | | 9/1990 | Phillips |
| 4,964,839 A | * | 10/1990 | Gloor ................... 464/29 |
| 5,041,131 A | * | 8/1991 | Nagase .................. 623/3.26 |
| 5,112,349 A | * | 5/1992 | Summers et al. ......... 623/3.15 |
| 5,163,910 A | | 11/1992 | Schwartz et al. |
| 5,300,112 A | * | 4/1994 | Barr .................... 623/3.15 |
| 5,678,306 A | * | 10/1997 | Bozeman et al. ......... 29/888.025 |
| 5,692,882 A | | 12/1997 | Bozeman, Jr. et al. |
| 5,741,234 A | | 4/1998 | Aboul-Hosn |
| 5,746,709 A | | 5/1998 | Rom et al. |
| 5,746,758 A | * | 5/1998 | Nordgren et al. ........ 606/159 |
| 5,776,190 A | * | 7/1998 | Jarvik .................. 600/16 |
| 5,810,088 A | | 9/1998 | Lamirand et al. ........ 166/377 |
| 5,851,174 A | * | 12/1998 | Jarvik et al. ............ 600/16 |
| 5,888,241 A | * | 3/1999 | Jarvik .................. 600/16 |
| 5,911,685 A | * | 6/1999 | Siess et al. ............. 600/16 |
| 5,947,892 A | * | 9/1999 | Benkowski et al. ....... 600/16 |
| 5,957,672 A | * | 9/1999 | Aber .................... 417/423.12 |
| 6,083,260 A | | 7/2000 | Aboul-Hosn |
| 6,086,570 A | | 7/2000 | Aboul-Hosn et al. |
| 6,093,001 A | * | 7/2000 | Burgreen et al. ........ 417/423.8 |
| 6,113,536 A | | 9/2000 | Aboul-Hosn et al. |
| 6,123,659 A | * | 9/2000 | le Blanc et al. ......... 600/16 |
| 6,123,725 A | | 9/2000 | Aboul-Hosn |
| 6,152,704 A | | 11/2000 | Aboul-Hosn et al. |
| 6,176,822 B1 | * | 1/2001 | Nix et al. .............. 600/17 |
| 6,176,848 B1 | * | 1/2001 | Rau et al. .............. 604/264 |
| 6,210,133 B1 | | 4/2001 | Aboul-Hosn et al. |
| 6,210,397 B1 | | 4/2001 | Aboul-Hosn et al. |
| 6,217,541 B1 | * | 4/2001 | Yu ...................... 604/9 |
| 6,228,063 B1 | | 5/2001 | Aboul-Hosn |
| 6,234,960 B1 | | 5/2001 | Aboul-Hosn et al. |
| 6,245,007 B1 | * | 6/2001 | Bedingham et al. ....... 600/16 |
| 6,287,319 B1 | | 9/2001 | Aboul-Hosn et al. |
| 6,295,877 B1 | | 10/2001 | Aboul-Hosn et al. |
| 6,336,939 B1 | * | 1/2002 | Yamazaki et al. ........ 623/3.13 |
| 6,346,120 B1 | * | 2/2002 | Yamazaki et al. ........ 623/3.13 |
| 6,395,026 B1 | | 5/2002 | Aboul-Hosn et al. |
| 6,532,964 B2 | | 3/2003 | Aboul-Hosn et al. |
| 6,613,008 B2 | | 9/2003 | Aboul-Hosn et al. |
| 6,709,418 B1 | | 3/2004 | Aboul-Hosn et al. |
| 7,022,100 B1 | * | 4/2006 | Aboul-Hosn et al. ...... 604/6.11 |
| 2003/0023201 A1 | | 1/2003 | Aboul-Hosn et al. |
| 2003/0205233 A1 | | 11/2003 | Aboul-Hosn et al. |

FOREIGN PATENT DOCUMENTS

| | | |
|---|---|---|
| DE | 196 22 335 A1 | 12/1997 |
| EP | 0 916 359 | 5/1999 |
| WO | WO 89/05164 | 6/1989 |
| WO | WO 99/02204 | 1/1999 |
| WO | WO 00/12148 | 3/2000 |
| WO | WO 00/18448 | 4/2000 |
| WO | WO 00/19097 | 4/2000 |
| WO | WO 00/37139 | 6/2000 |
| WO | WO 00/69489 | 11/2000 |
| WO | WO 01/78807 | 10/2001 |

OTHER PUBLICATIONS

Online encyclopedia article "Ventricular assist device, List of implantable VAD devices" accessed Jan. 12, 2010. http://en.wikipedia.org/wiki/Ventricular_assist_device.*

* cited by examiner

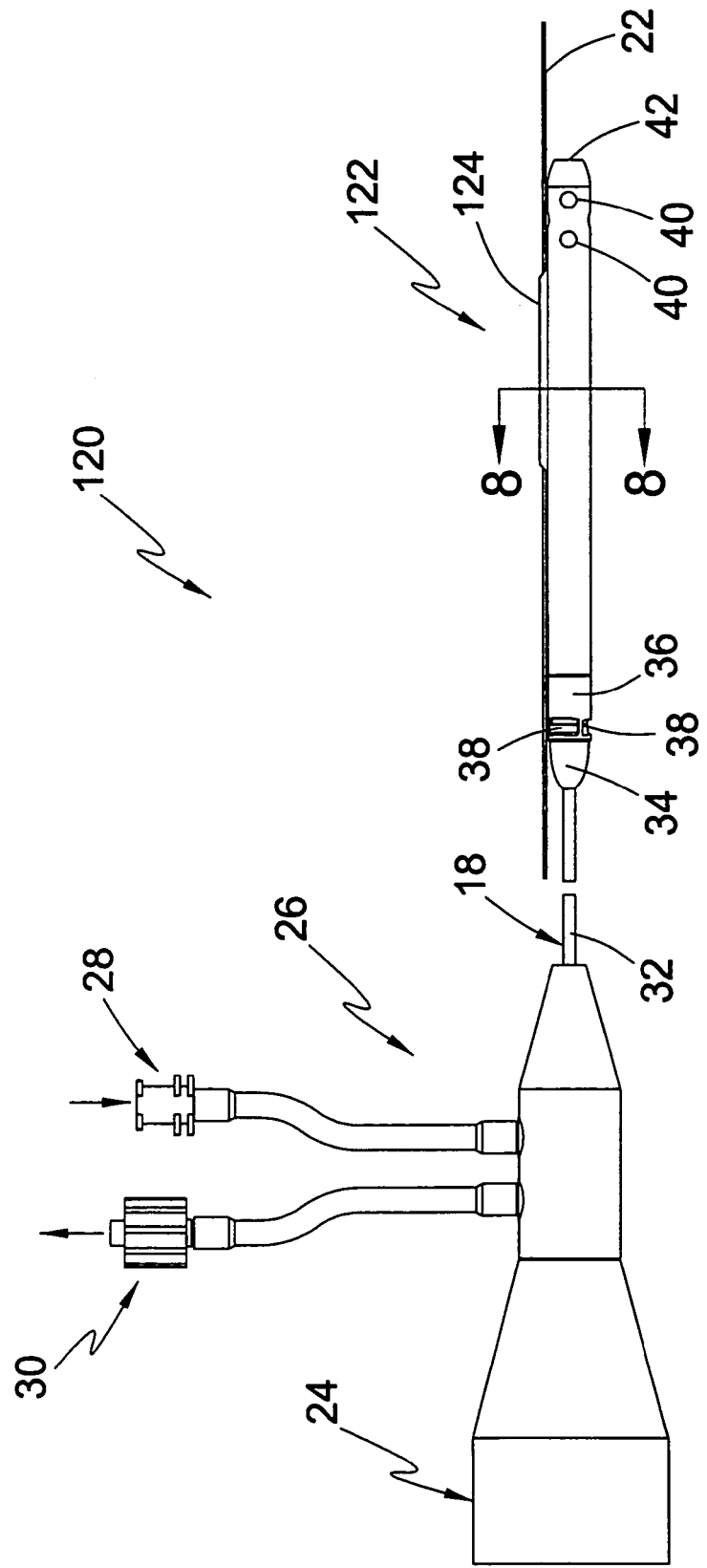

GUIDABLE INTRAVASCULAR BLOOD PUMP AND RELATED METHODS

RELATED APPLICATIONS

This application is a divisional of U.S. patent application Ser. No. 10/070,178, filed Jul. 19, 2002, now U.S. Pat. No. 7,022,100 which claims the benefit of PCT/US00/24515 filed Sep. 1, 2000, which claims the benefit of provisional U.S. patent application Ser. No. 60/152,249 filed Sep. 3, 1999.

FIELD OF THE INVENTION

The present invention relates generally to blood pumps and, more particularly, to an improved intravascular blood pump having a guide mechanism which provides the ability to selectively guide the intravascular pump to a desired location within a patient's circulatory system.

DESCRIPTION OF RELATED ART

Over the years, various types of blood pumps have been developed for the purpose of augmenting or replacing the blood pumping action of damaged or diseased hearts. Blood pumps are commonly used in three situations: (1) for acute support during cardio-pulmonary operations; (2) for short-term support while awaiting recovery of the heart from surgery; or (3) as a bridge to keep a patient alive while awaiting heart transplantation. The pumps may be designed to provide right and/or left ventricular assist, although left ventricle assist is the most common application in that it is far more common for the left ventricle to become diseased or damaged than it is for the right ventricle.

Blood pumps must provide leak-free operation and must avoid contamination of the fluid by the pump components and the external environment. Such pumps must also pump the fluid at a suitable rate without applying excessive Reynolds shear stress to the fluid. It is well known to those skilled in the art that lysis or cell destruction may result from application of shear stress to cell membranes. Red blood cells are particularly susceptible to shear stress damage as their cell membranes do not include a reinforcing cytoskeleton to maintain cell shape. Lysis of white blood cells and platelets also occurs upon application of high shear stress. Lysis of red blood cells can result in release of cell contents which trigger subsequent platelet aggregation. Sublytic shear stress leads to cellular alterations and direct activation and aggregation of platelets and white blood cells.

Intravascular blood pumps comprise miniaturized blood pumps capable of being percutaneously or surgically introduced into the vascular system of a patient, typically to provide left and/or right heart support. One type of intravascular pump is an axial flow blood pump comprising a cable-mounted rotor surrounded by a protective shroud. The pump, along with the rotor and shroud, are mounted at the end of an elongated flexible catheter. The catheter is inserted into the aorta from a remote entry point, such as an incision below the groin that provides access into a femoral artery. The catheter then passes through the descending aorta until it reaches the ascending aorta, near the heart. The catheter device encloses a rotating drive cable which is coupled to the impeller blade at one end, and which emerges from the exposed end of-the catheter, near the patient's groin, at the other end. When the exposed end of the drive cable is mechanically rotated, using a device located outside the patient's body, it conveys the rotational force through the length of the catheter, causing the impeller to spin at high speed near the heart. This type of blood pump finds particular application in providing ventricular assist during surgery or providing temporary bridging support to help a patient survive a crisis.

While generally effective in providing ventricular assisting functions, prior art intravascular blood pumps nonetheless suffer various drawbacks. A significant drawback is that prior art intravascular blood pumps are difficult to guide into the appropriate position within the circulatory system of a patient. This is due largely to the fact that the elongated catheter is incapable of providing the degree of control necessary to easily negotiate the pump through the tortuous pathways leading up to and into the heart. When attempting to place the blood pump in a trans-valvular configuration (with the inlet in the left ventricle and the pump outlet in the ascending aorta), the natural tendency of the catheter to stay straight may cause the pump to be inadvertently placed in the carotid ostia, which can be dangerous if the pump is operated to withdraw blood from the brain.

To overcome these difficulties, certain guide mechanisms may be employed to assist the physician placing the pump in the appropriate position within the circulatory system. One type of supplemental guide mechanism is a guide catheter. Guide catheters are designed with certain guidability characteristics such that physicians can selectively position them within the vasculature or heart with relative ease. A central lumen is provided within the guide catheter such that the intravascular pump may be introduced therein and guided while it is advanced towards the predetermined circulatory site. While generally effective at providing a guiding feature for such intravascular blood pumps, employing such supplemental guide mechanisms is nonetheless disadvantageous in that they consume valuable space within the vessels. A guide catheter, for example, would necessarily be larger in diameter than the diameter of the pump and protective shroud in order to provide adequate passage of those components. As will be appreciated, this restricts the amount of space available for blood to flow within the particular vessel, and increases the size of the required puncture wound for accessing the vessel.

The present invention is directed at eliminating and/or reducing the effects of the foregoing drawbacks of prior art intravascular blood pumps.

SUMMARY OF THE INVENTION

The present invention overcomes the drawbacks of the prior art by providing an improved intravascular blood pump equipped with integrated features for selectively guiding the intravascular blood pump to a predetermined location in the patient's circulatory system, i.e. heart and/or vasculature. In so doing, the intravascular blood pump of the present invention eliminates the need for supplemental guiding mechanisms, such as a separate, large diameter guide catheter as used in the prior art.

In a first broad aspect of the present invention, an intravascular blood pump system is provided comprising an intravascular blood pump having a cannula coupled thereto and an "over-the-wire" type guide mechanism for selectively positioning the intravascular blood pump and cannula at a predetermined location within the circulatory system of a patient. To accomplish this, a central lumen is formed through at least a portion of the intravascular blood pump system such that a guide element, such as a guide wire, may be progressed therethrough and advanced to the predetermined location in the circulatory system of the patient. After the guide element is advanced to this desired location, the intravascular blood pump and cannula may thereafter be advanced along the guide element to the desired location.

In a second broad aspect of the present invention, an intravascular blood pump system is provided comprising an intravascular blood pump having a cannula coupled thereto and a "side-rigger" or "rapid exchange" type guide mechanism for selectively positioning the intravascular blood pump and cannula at a predetermined location within the circulatory system of a patient. To accomplish this, a side lumen is formed along a length of at least one of the intravascular blood pump and the cannula. A guide element, such as a guide wire, may be advanced to the predetermined location in the circulatory system of the patient. After the guide element is advanced to this desired location, the intravascular blood pump and cannula may thereafter be advanced along the guide element to the desired location.

In a third broad aspect of the present invention, an intravascular blood pump system is provided comprising an intravascular blood pump having a cannula coupled thereto and a "guide catheter" type guide mechanism for selectively positioning the intravascular blood pump and cannula at a predetermined location within the circulatory system of a patient. The pump system of this broad aspect includes a conduit assembly and a separate pump assembly. The conduit assembly includes a guide catheter, a rotor shroud, and a cannula, with the cannula and guide catheter disposed on either side of the rotor shroud. The pump assembly includes a rotor, a drive member coupled to the rotor, and a pump disposed between the rotor and the drive member. The guide catheter is dimensioned to receive and guide the pump assembly to the point where the rotor docks within the rotor shroud so as to form an operational blood pump. This configuration allows the conduit assembly to be precisely and efficiently guided into a desired position within the body through the use of conventional guiding techniques well known in interventional cardiology. The pump assembly may thereafter be introduced into and guided within the conduit until the pump assembly is docked within the rotor shroud. This dual construction arrangement provides improved placement of the pump assembly by using the conduit as a guiding mechanism.

The foregoing broad aspects of the present invention may be manifested according to the following recitations:

According to a first broad recitation of the present invention, an intravascular blood pump system is provided comprising an intravascular blood pump having a cannula coupled thereto, and a guide mechanism adapted to guide the intravascular blood pump and cannula to a predetermined location within the circulatory system of a patient.

In a further embodiment, the intravascular blood pump includes a rotor, a shroud for receiving the rotor, and a drive cable coupled to the rotor for driving the rotor within the shroud.

In a further embodiment, the cannula is coupled to the shroud of the intravascular blood pump.

In a further embodiment, the guide mechanism comprises a guide catheter coupled to the shroud.

In a further embodiment, the guide catheter may be used to guide the shroud and cannula to the predetermined location within the circulatory system of the patient, after which point the rotor and drive cable of the intravascular blood pump may be docked-within the shroud for pump operation.

In a further embodiment, the drive cable sheath is provided having a central lumen for receiving the drive cable, and wherein a purge fluid delivery system is coupled to the drive cable sheath to deliver purge fluid to the rotor.

In a further embodiment, the drive cable sheath includes at least one side lumen for delivering the purge fluid towards the rotor.

In a further embodiment, a portion of the purge fluid is delivered through the at least one side lumen and past the rotor, and a portion of purge fluid is rerouted back from the rotor through the central lumen of the drive cable.

In a further embodiment, a perfusion assembly is provided communicatively coupled to the guide catheter for selectively rerouting blood from within the guide catheter to a point downstream from the introduction site of the guide catheter into the vasculature of the patient.

In a further embodiment, the perfusion assembly includes a first conduit communicatively coupled to the guide catheter, a second conduit dimensioned to be introduced into the vasculature of the patient, and a selectively operable valve disposed in between the first conduit and the second conduit.

In a further embodiment, a blood pressure detection mechanism is provided to detect the pressure of the blood proximate at least one of the intravascular blood pump and cannula.

In a further embodiment, the blood pressure detection mechanism comprises at least one of fluid filled column disposed within at least a portion of the cannula, a piezoelectric element coupled to at least one of the intravascular blood pump and cannula, and a strain gauge coupled to at least one of the intravascular blood pump and cannula.

In a further embodiment, the blood pressure detection mechanism involves calculating blood pressure based on the relationship between the torque and motor current of a motor used to drive the rotor.

In a further embodiment, the guide mechanism comprises a guide element disposed at least partially within the cannula.

In a further embodiment, the guide element comprises a guide wire for passage through a side lumen formed in the cannula.

In a further embodiment, the guide element comprises a selectively deformable element disposed at least partially within the cannula.

In a further embodiment, the intravascular blood pump and cannula may be selectively advanced to the predetermined location within the vasculature of the patient by first passing the guide wire to the predetermined location and thereafter sliding the intravascular blood pump and cannula along the guide wire to the predetermined location.

In a further embodiment, the guide element comprises a guide wire for passage through a lumen extending through the drive cable and rotor.

In a further embodiment, the intravascular blood-pump and cannula may be selectively advanced to the predetermined location within the vasculature of the patient by first passing the guide wire to the predetermined location and thereafter sliding the intravascular blood pump and cannula along the guide wire to the predetermine location.

In a further embodiment, the guide mechanism further includes guide element for passage through the guide catheter-to facilitate placement of the shroud and the cannula at the predetermined location within the vasculature of the patient.

In a further embodiment, the guide mechanism further includes a guide element for passage through a side lumen formed along at least a portion of the guide catheter.

In a further embodiment, the guide element comprises at least one of a guide wire and a balloon catheter.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 7 is side view of the guidable intravascular blood pump system of the type shown in FIG. 6 including a motor coupler and purge fluid delivery system according to an exemplary embodiment of the present invention;

DETAILED DESCRIPTION OF THE INVENTION

Illustrative embodiments of the invention are described below. In the interest of clarity, not all features of an actual implementation may be described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort night be complex and time-consuming, but would nevertheless be a routine undertaking for those of ordinary skill in the art having the benefit of this disclosure.

The present invention involves an intravascular pump system for use in a number of broad ranging applications involving the augmentation of blood flow within the circulatory system of a patient. As will be described below, the intravascular blood pump system of the present invention overcomes the drawbacks of the prior art by providing a guide mechanism as part of the intravascular blood pump. This advantageously allows the intravascular blood pump to be selectively guided to a predetermined location within the circulatory system of a patient without the need for bulky supplemental guide mechanisms, such as a separate guide catheter.

The intravascular pump assembly of the present invention is particularly suited for trans-valvular use, such as for left and/or right ventricular assist procedures. By way of example only, such ventricular assist procedures may be employed in cardiac operations including, but not limited to, coronary bypass graft (CABG), cardiopulmonary bypass (CPB), open chest and closed chest (minimally invasive) surgery, bridge-to-transplant and/or failure-to-wean-from-bypass situations. It is to be readily understood, however, that the intravascular blood pump assembly and methods of the present invention are not to be limited to such applications. Moreover, while illustrated and described largely with reference to left-heart assist applications, it is to be readily understood that the principles of the present invention apply equally with regard to right-heart assist application, which are contemplated as within the scope of the present invention. These and other variations and additional features will be described throughout.

Figure 1:
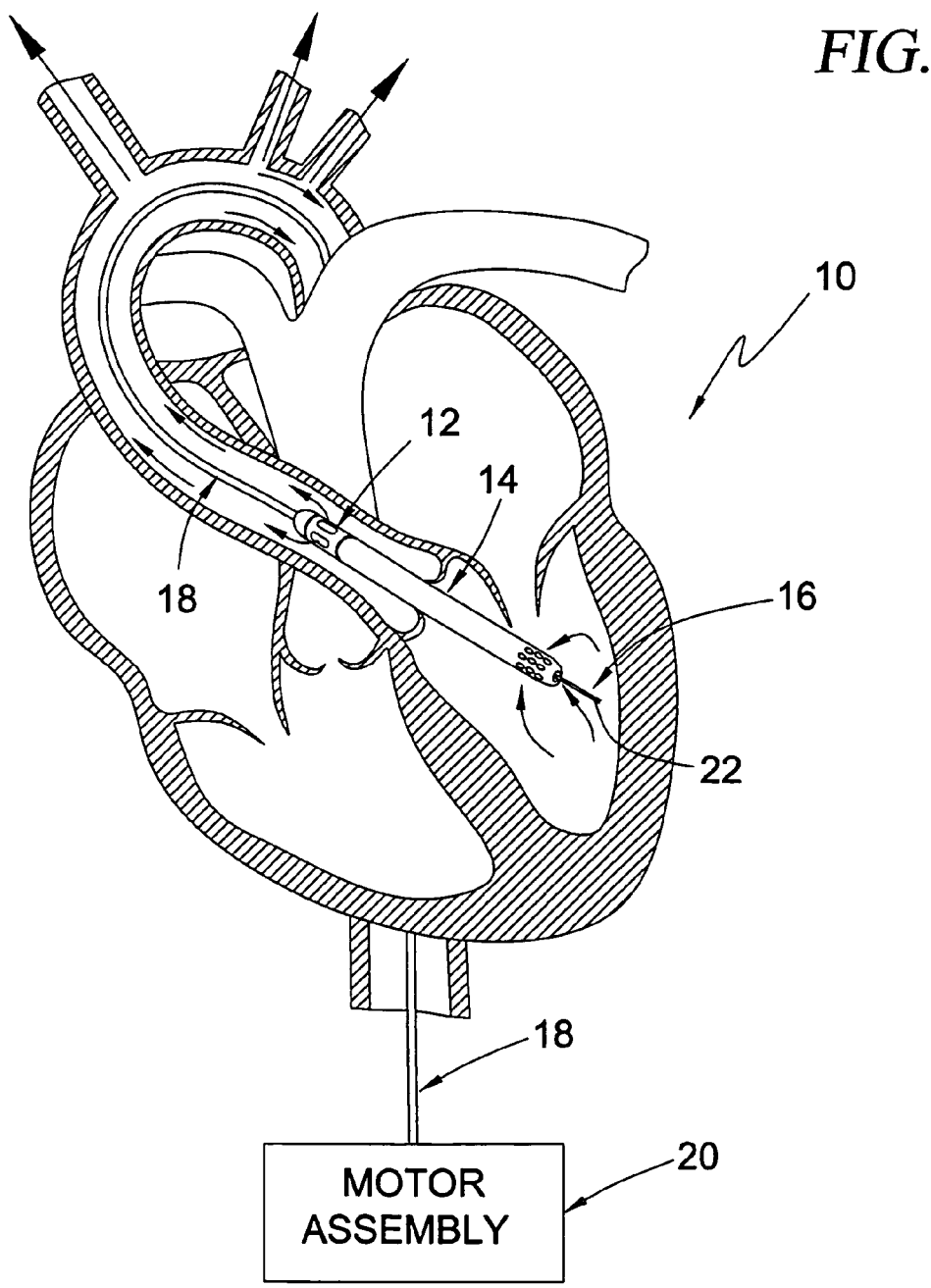
FIG. 1 is a partial sectional view of a human heart illustrating an intravascular blood pump system having an "over-the-wire" type guide mechanism according to a first broad aspect of the present invention positioned, by way of example, in a trans-valvular configuration to provide left-heart assist.

Referring to FIG. 1, shown is a guidable intra-vascular blood pump system 10 according to a first broad aspect of the present invention shown, by way of example only, in a left-heart assist configuration within a human heart. The system 10 includes an intravascular blood pump 12, a cannula 14, and an "over-the-wire" type guide mechanism 16. A drive cable assembly 18 and a motor assembly 20 are provided to drive the intravascular blood pump 12. The "over-the-wire" guide mechanism 16 comprises a suitable guide element dimensioned to pass slideably through a central lumen extending through the drive cable 18, blood pump 12, and cannula 14. Suitable guide elements may include any number of conventional guiding devices, including but limited to those employed in cardiology. By way of example only, the guide element is shown as a guide wire 22. According to the present invention, the "over-the-wire" guide mechanism 16 provides the ability to selectively guide the blood pump 12 and cannula 14 to a predetermined position in the circulatory system of a patient, such as the trans-valvular position shown.

To accomplish this, the guide wire 22 is first introduced into the vascular system of a patient through any suitable access point, such as through the use of the well known Seldinger technique. The guide wire 22 can then be advanced within the patient to a desired location within the circulatory system of the patient. This may be done using the control features of the guide wire 22 itself, or may be facilitated through the use of any number of supplemental guidance mechanisms or techniques to ensure the proper and efficient placement of the guide wire 22. Such supplemental guidance techniques may include, but are not necessarily limited to, guide catheters and/or techniques involving ultra-sound or flouroscopy. Once the guide wire 22 is positioned at the desired location (such as in left ventricle as shown), the blood pump 12 and cannula 14 may thereafter be advanced along the guide wire 22 and positioned in the trans-valvular configuration shown. Under the operation of the motor assembly 20, the blood pump 12 may be used for left-heart assist by selectively withdrawing blood from the left ventricle (through the interior of the cannula 14) for delivery outward through outflow apertures formed in the blood pump 12. This outflow from the blood pump 12 flows along the exterior of the drive cable assembly 18 in a substantially axial fashion for arterial coupler 24 and, as will be described in greater detail below, a purge fluid distribution throughout the body.

Figure 2:
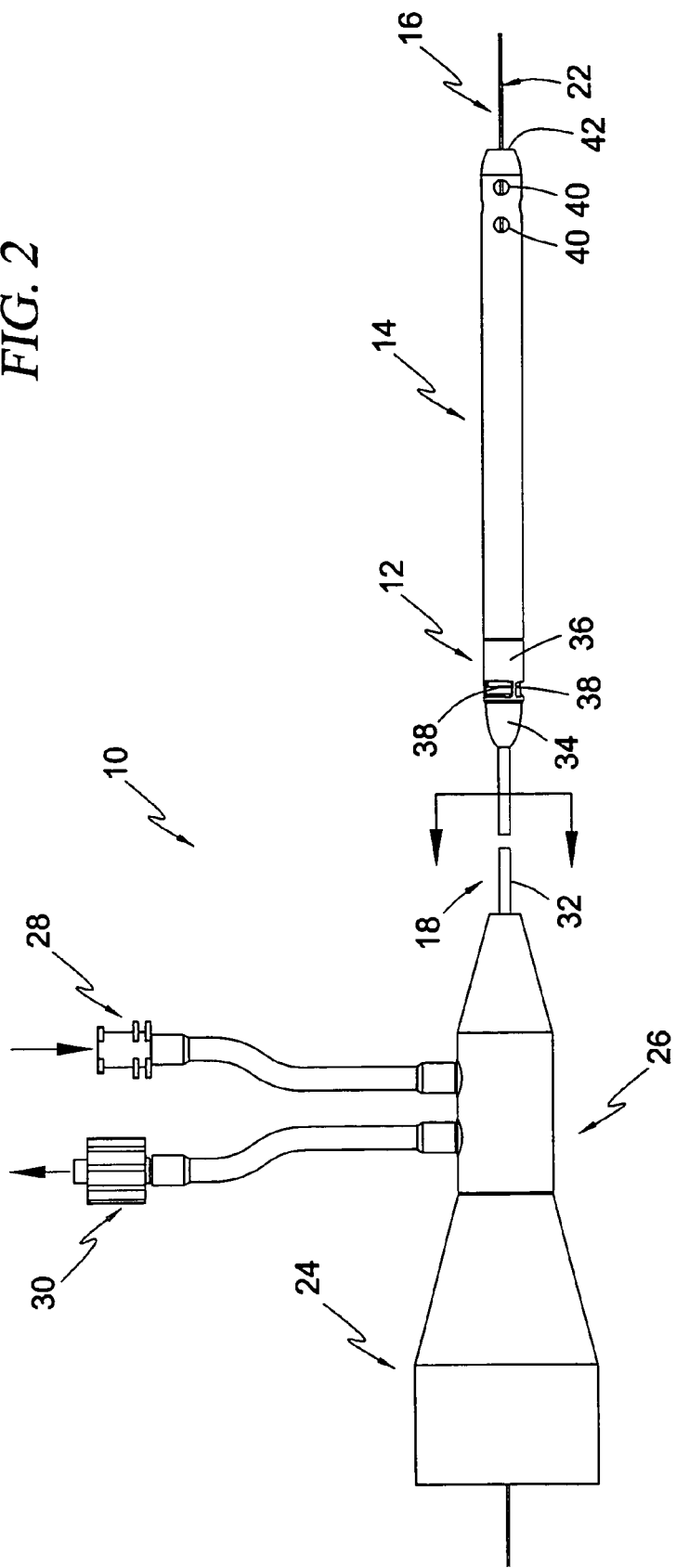
FIG. 2 is side view of the guidable intravascular blood pump system of the type shown in FIG. 1 including a motor coupler and purge fluid delivery system according to an exemplary embodiment of the present invention.

Referring to FIGS. 2-5, an exemplary embodiment of the intravascular blood pump system 10 of FIG. 1 will now be described. As shown in FIG. 2, the intravascular blood pump system 10 includes a motor delivery system 26 for providing a two-way fluid flow within the drive cable assembly 18 during pump operation. The purge fluid delivery system 26 includes a fluid inlet conduit 28 for introducing pressurized purge fluid from a fluid source (not shown) for delivery into the blood pump 12, and a fluid outlet conduit 30 to withdraw a return flow of purge fluid from the blood pump 12. The motor coupler 24 establishes a mechanical connection between a motor (not shown) and a drive cable (not shown) for providing motive force to the blood pump 12 for pump operation. The drive cable assembly 18 includes a drive cable sheath 32 which, in addition to serving a purge fluid delivery function, also serves as a protective housing for the drive cable (not shown). Although shown in broken form for clarity, it will be appreciated that the drive cable assembly 18 (and all components thereof) may be provided in any suitable length sufficient for intravascular applications. That is to say, the length of the drive cable assembly 18 must be enough to reach between the motor coupler 24 and purge fluid delivery system 26, located outside the patient, and the desired location within the patient's circulatory system where the blood pump 12 is to be positioned.

The intravascular blood pump 12 is shown (by way of example only) as an axial flow intravascular blood pump. The blood pump 12 includes pump body 34, a rotor shroud 36 having flow ports 38, and an internally disposed rotor (not shown) having a shaft rotatably disposed within the pump body 34 and an impeller rotatably disposed within the rotor shroud 36. The cannula 14 is fixedly attached to the rotor shroud 36 and nay extend any suitable length therefrom depending upon the particular intravascular application. The cannula 14 preferably includes a plurality of ports or fenestrations 40 about its distal region, as well as an end port 42, which allow for the ingress or egress of blood into or from the cannula 14 depending upon the operation of the blood pump 12. That is to say, if the pump 12 is configured for left-heart assist as shown in FIG. 1, then the ports 40, 42 will allow the ingress of blood into the cannula 14 from the left ventricle. If, on the other hand, the blood pump 12 is configured for right-heart assist (i.e. with the pump 12 in the right atrium and the distal end of the cannula 14 located within the pulmonary artery), then the ports 40, 42 will allow the egress of blood from the cannula 14 into the pulmonary artery. (Details on right-heart assist applications will be discussed in greater detail below.) The pump 12 and cannula 14 may be dimensioned to any suitable diameter for intravascular applications. For example, the range of sizes may include, but is not necessarily limited to, 9 French to 30 French, although the range is more preferably from 14 French to 24 French, and most preferably from 18 French to 20 French.

The "over-the-wire" type guide mechanism 16 includes the guide wire 22 and, as will be explained in greater detail below, a central lumen extending through the cannula 14, blood pump 12, drive cable assembly 18, purge fluid delivery system 26, and motor coupler 24. As noted above, the central lumen is dimensioned to slideably receive the guide wire 22 such that the blood pump 12 and cannula 14 may be slideably advanced along the guide wire 22 to a desired location within the circulatory system of a patient after the guide wire 22 has been so positioned using conventional guidance techniques. It is to be readily understood that, while shown as a conventional guide wire 22, the guide element forming part of the guide mechanism 16 of the present invention nay include any number of well known guidance mechanisms depending upon the application, including but not limited to balloon catheters, imaging wires, and guide catheters dimensioned to be slideably received through the central lumen. For example, although not appropriate for retrograde progression (such as the left-heart application shown in FIG. 1), a balloon catheter may be a suitable guidance mechanism for a right-heart assist application. In such a case, the balloon may be inflated and used as a "sail" to direct the catheter to a desired location (such as the pulmonary artery), after which point the blood pump 12 and cannula 14 can be advanced over the catheter to a trans-valvular configuration with the blood pump 12 in the right atrium and the ports 38, 40 of the cannula 14 in the pulmonary artery.

Figure 3:
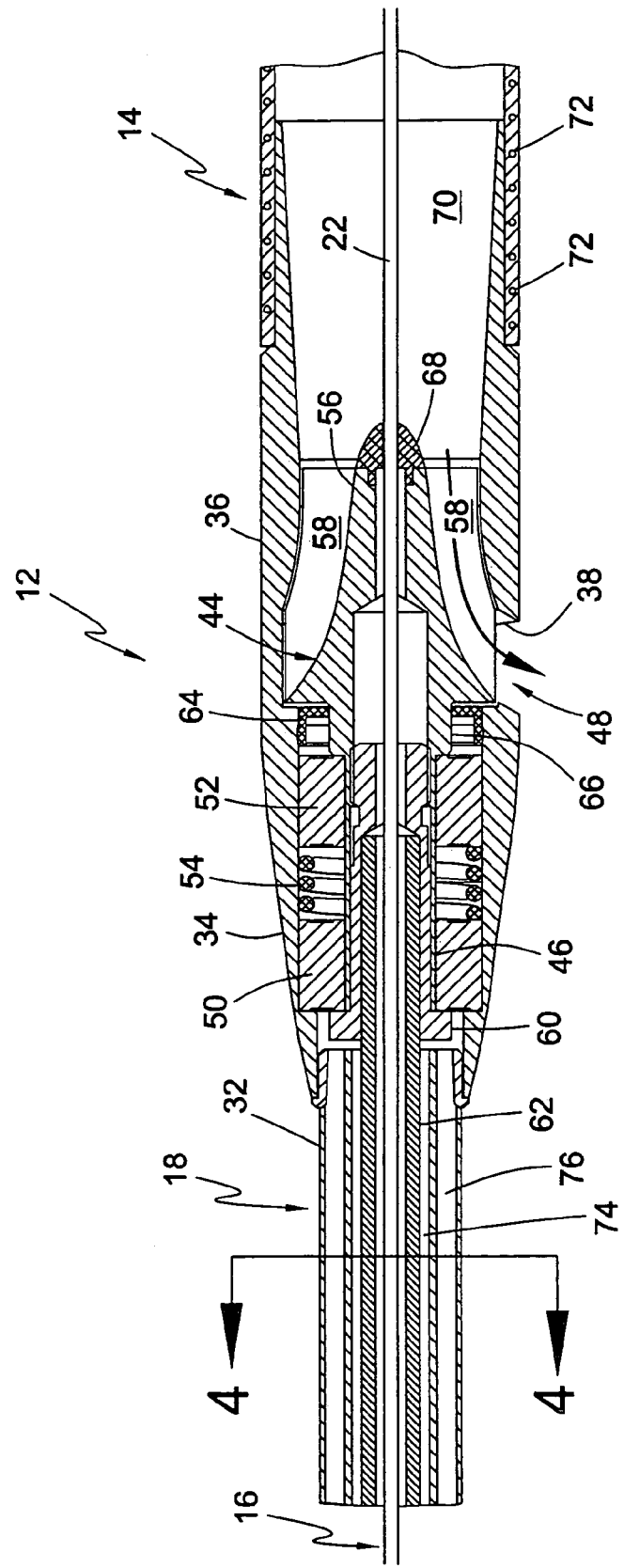
FIG. 3 is a cross-sectional view illustrating an exemplary construction of the blood pump, drive cable assembly, and cannula of the intravascular blood pump system according to the first broad aspect of the present invention.
Figure 4:
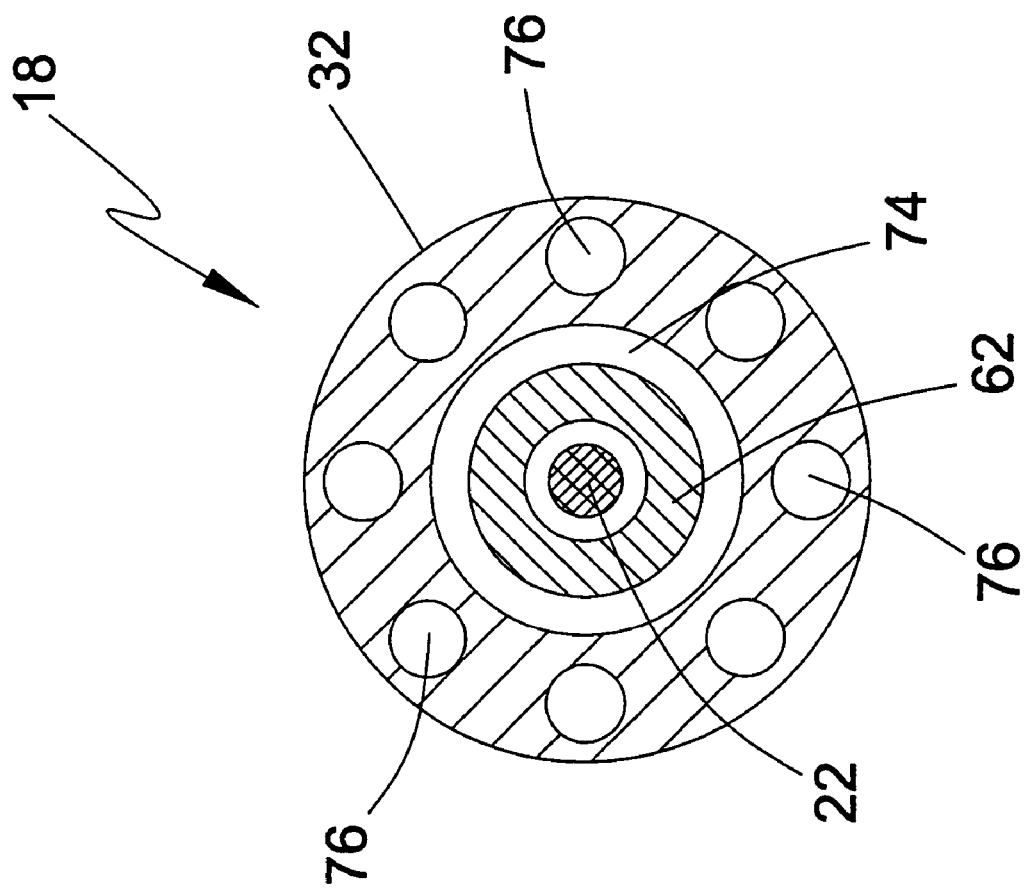
FIG. 4 is a cross-sectional view taken along lines 4-4 of FIG. 3 illustrating an exemplary construction of the drive cable assembly and guide mechanism according to the first broad aspect of the present invention.

FIGS. 3 and 4 further detail the construction of the blood pump 12, cannula 14, drive cable assembly 18, and "over-the-wire" guide mechanism 16. The blood pump 12 includes a rotor 44 having a shaft 46 and an impeller 48. The shaft 46 is rotatably disposed within the pump body 34 via a bearing pack comprising, by way of example, ball bearing assemblies 50, 52 and spring 54. Ball bearings assemblies 50, 52 are well known in the art, each comprising an inner race which rotates along with the rotor shaft 46, an outer race which remains in a static and fixed position against the inner surface of the pump body 34, and a plurality of ball bearings disposed between the inner and outer races. The spring 54 biases each bearing assembly 50, 52 axially away from one another to reduce axial play during pump operation. The shaft 46 is generally hollow and dimensioned to receive a cable adapter 60 therein for the purpose of coupling the rotor 44 to a drive cable 62 forming part of the drive cable assembly 18. The drive cable 62 may be secured to the cable adapter 60 in any number of suitable fashions, including but not limited to the use of adhesives, crimping, and laser welding. These same techniques may be used to secure the cable adapter 60 within the shaft 46 of the rotor 44. A radial seal 64 is provided in between the wall of the pump body 34 and a distal stepped region 66 on the rotor shaft 46, the function of which will be described below.

The impeller 48 includes a hub 56 and a plurality of blades 58 extending therefrom. The hub 56 is generally conical and, according to the first broad aspect of the present invention, is hollow throughout to form part of the central lumen of the guide mechanism 16. In this regard, the hub 56 is preferably provided with a gasket or seal member 68 at its distal tip. The seal member 68 may be made of any suitable sealing material (including but not limited to silicone) such that the pump 12 and cannula 14 may be easily progressed along the guide wire 22 for delivery to a desired circulatory site. The seal member 68 should also be robust enough to prevent the ingress of blood into the interior of the rotor hub 56 during pump operation, whether the guide wire 22 remains in place or is fully withdrawn. The blades 58 are dimensioned to reside in close tolerance with the interior surface of the shroud 36. In operation, the blades 58 impart both an axial and radial vector on the blood which causes it to flow outward through the flow ports 38 formed in the shroud 36. As used herein, the term "axial flow" is deemed to include flow characteristics like that shown in FIG. 3, which include both an axial and slight radial component. It is to be readily appreciated that, although shown as an axial flow type, blood pump 12 may comprise any number of suitable types of intravascular blood pumps, including but not limited to so-called "mixed flow" intravascular blood pumps without departing from the scope of the present invention.

The cannula 14 is coupled at its proximal end to the rotor shroud 36. This may be accomplished in any number of fashions, including but not limited to the use of adhesives. This may also be facilitated by dimensioning the shroud 36 to include a narrow inlet region 70 capable of being received flushly within the proximal end of the cannula 14. The inlet region 70 of the shroud 36 should preferably have a tapered interior surface for establishing a smooth flow transition between the cannula 14 and the region containing the impeller blades 58. Although shown as a single integral element, it is to be understood that the pump-body 34 and shroud. 36 may comprise two separate (and sometimes separable) components, the significance of which will become apparent below. The pump body 34 and shroud 36 may be constructed from any number of suitable materials, including but not limited to stainless steel or other medical grade compositions or alloys. The cannula 14 may also be constructed from any number of suitable materials, including but not limited to medical grade plastics. As shown, the cannula 14 may also be fortified with spiral-wound reinforcement wire 72 within the walls of the cannula 14.

The drive cable assembly 18 includes the drive cable 62 and the drive cable sheath 32. The drive cable 62 is coupled to the rotor 44 via the cable adapter 60. The drive cable sheath 32 includes a central lumen 74 and a plurality of side lumens 76. The central lumen 74 serves as a protective covering for the drive cable 62. The central lumen 74, along with the side lumens 76, also forms part of the purge fluid delivery system 26 shown above in FIG. 2, which will be described in greater detail below. The side lumens 76 are provided in fluid communication with the fluid inlet conduit 28, while the central lumen 74 is provided in fluid communication with the fluid outlet conduit 30. The side lumens 76 are thus configured to deliver purge, fluid into the pump 12, while the central lumen 74 is configured to transport purge fluid away from the pump 12 along the length of the drive cable 62.

The pressurized purge fluid within the side lumens 76 may take one of two flow paths upon entry into the pump 12. One flow path passes through the interior of the pump 12 and onward past the radial seal 64 to prevent the ingress of blood into the pump body 34 during pump operation. More specifically, the purge fluid flows distally around the cable adapter 60, through the ball bearing assemblies 50, 52, and onward past the radial seal 64. This egress of purge fluid past the radial seal 64 can be controlled to effectively thwart the ingress of blood past the radial seal 64, which might otherwise cause clotting and/or pump damage. The other flow path is directed back out the central lumen 74 for delivery to the fluid outlet conduit 30. In so doing, this flow path bathes the components of the pump 12 and/or drive cable 62 and thereby reduces frictional heating within the pump 12 and/or the central lumen 74 of the sheath 32 during pump operation.

The "over-the-wire" guide mechanism 16 includes a central lumen through which the guide wire 22 may extend for the purpose of slideably advancing the blood pump 12 and cannula 14 into a desired position within the circulatory system of a patient. In the embodiment shown, this central lumen is established by forming and co-aligning the individual central lumens within each of the drive cable 62, the cable adapter 60, the shaft 46 and hub 56 of the rotor 44, and the cannula 14. In this regard, the drive cable 62 is preferably of wound-wire construction having a central lumen formed therein. The central lumens within the cable adapter 60, rotor 44, and gasket 68 may be formed via machining or molding processes. These central lumens should preferably be sized such that they permit the slideable passage of the pump 12 and cannula 14 therealong, but do not interfere with or constrain the guide wire 22 to cause inadvertent rotation of the guide wire 22 during pump operation. As noted above, it is also contemplated to remove the guide wire 22 after the pump 12 and cannula 14 are properly positioned in the patient. In this case, the gasket or seal 68 on the hub 56 should be robust enough to reseal after the guide wire 22 is withdrawn and prevent the ingress of blood into the interior of the rotor 44.

Figure 5:
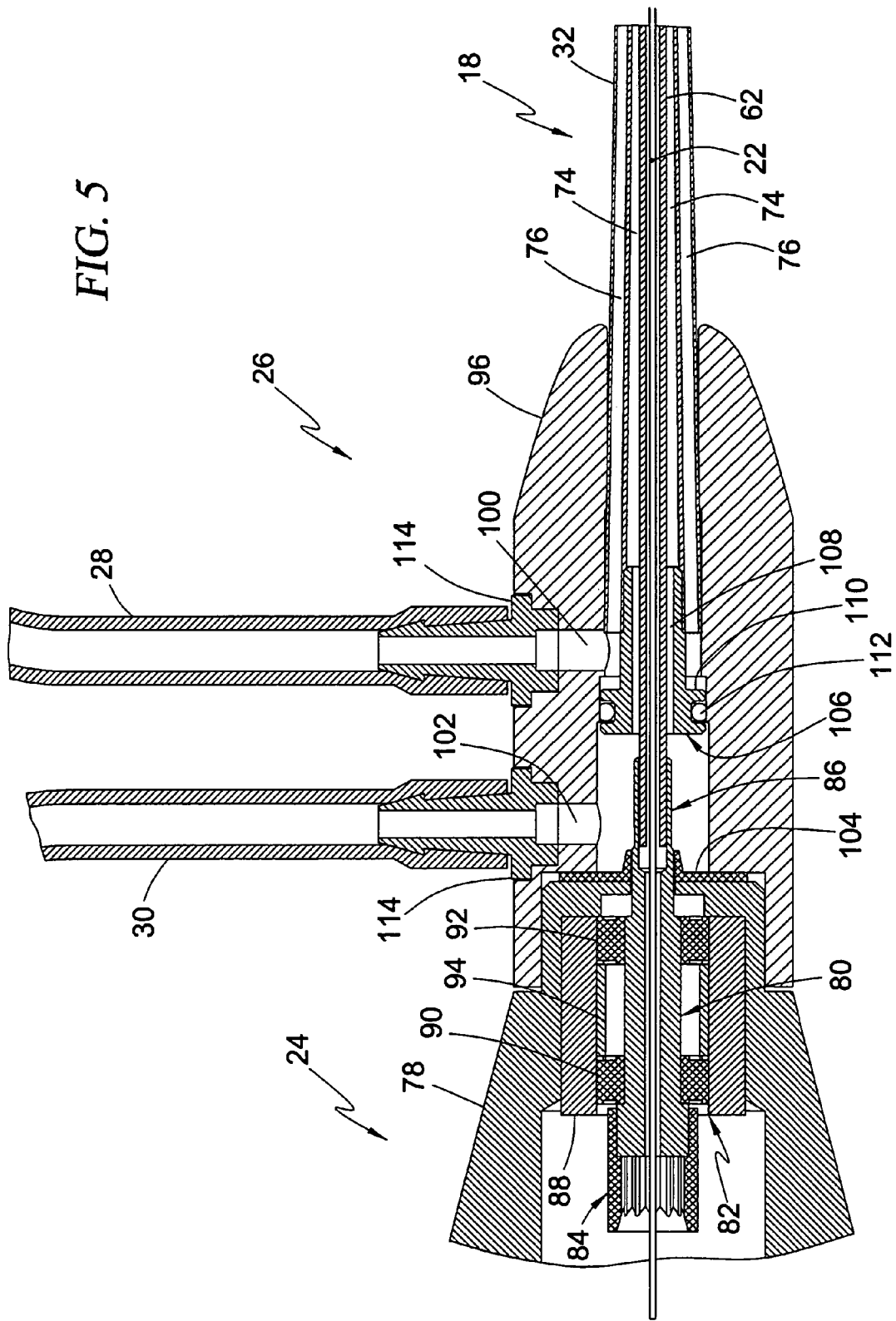
FIG. 5 is a cross-sectional view illustrating an exemplary construction of the motor coupler and purge fluid delivery system according to the first broad aspect of the present invention.

Referring to FIG. 5, the motor coupler 24 includes a housing 78, a drive shaft adapter 80, and a bearing assembly 82. The drive shaft adapter 80 includes a drive shaft coupler 84 dimensioned to receive a drive shaft of a motor (not shown), and a drive cable coupler 86 dimensioned to receive the drive cable 62. Any of a variety of attachment techniques may be employed to securely fasten the drive cable 62 to the drive cable coupler 86, including but not limited to adhesives, crimping, and laser welding. The drive shaft adapter 80 is rotatably disposed within the housing 78 by the bearing assembly 82. The bearing assembly 82 includes a sleeve 88 (which may alternatively be formed as an integral part of the housing 78) for retaining a pair of ball bearing assemblies 90, 92 and a spring 94 of the type described above. That is, each bearing assembly 90, 92 generally comprises an inner race which rotates along with the drive shaft adapter 80, an outer race which remains in a static and fixed position against the inner surface of the retaining sleeve 88, and a plurality of ball bearings disposed between the inner and outer races. The spring 94 is provided to bias each bearing assembly 90, 92 axially away from one another to reduce axial play during operation.

The purge fluid delivery system 26 includes a housing 96 having a central lumen 98, an inflow port 100, and an outflow port 102. The housing 96 is also dimensioned to matingly receive a portion of the motor coupler 24. In this regard, a seal element 104 is provided sandwiched in between the housing 96 and housing 78 and including an aperture which extends about the drive shaft adapter 80 as it exits the housing 78 to prevent the ingress of purge fluid into the motor coupler 24. A fluid guide structure 106 is also provided within the central lumen 98 for the purpose of separating the inflow and outflow ports 100, 102. The fluid guide structure 106 includes a central lumen 108 through which the drive cable 62 extends, and an elevated portion 110 that retains an O-ring 112 against the inner surface of the central lumen 98 of the housing 96. The drive cable sheath 32 is secured to the housing 96 such that the inflow port 100 is communicatively coupled to the side lumens 76, and the outflow port 102 is communicatively coupled to the central lumen 74. In this fashion, pressurized purge fluid may be introduced through the inflow port 100 via inflow conduit 28, and removed through the outflow port 102 via outflow conduit 30. By way of example, the inflow conduit 28 and outflow conduit 30 may be coupled to their respective ports 100, 102 via barbed connectors 114. Similarly, the inflow and outflow conduits 28, 30 may be equipped with any number of suitable connectors (such as those illustrated by way of example in FIG. 2) for establishing fluid communication with a source of pressurized fluid (not shown). The pressurized fluid source (not shown) may include, but is not necessarily limited to, the use of a syringe, an indeflator, a fluid delivery pump, or an accumulator arrangement to provide the requisite delivery of pressurized fluid. The purge fluid delivery system 26 thus provides a two-way transmission of purge fluid within the drive cable sheath 32 for the purposes of cooling the blood pump 12 and preventing the ingress of blood past the radial seal 64 and into blood pump 12.

Figure 6:
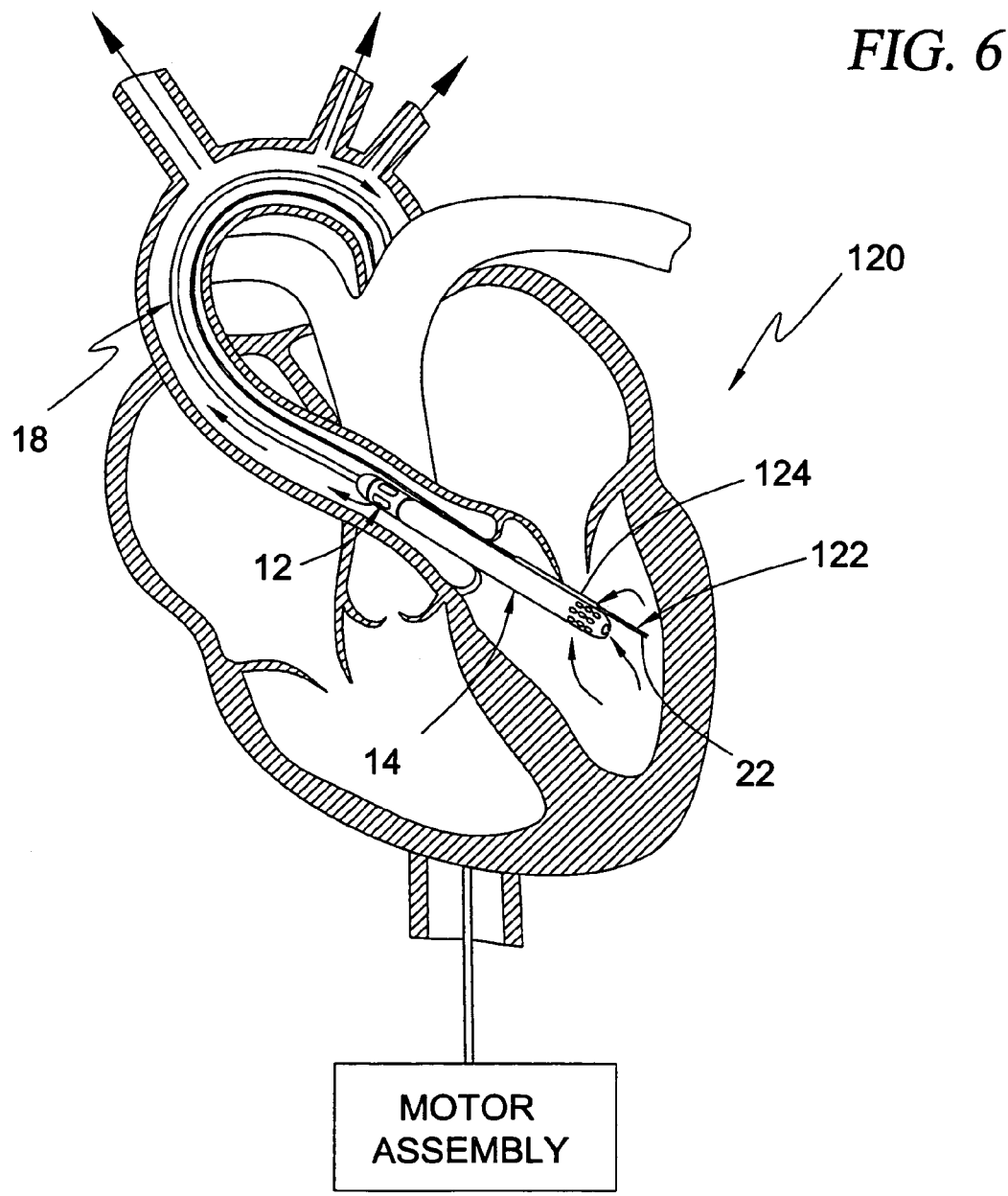
FIG. 6 is a partial sectional view of a human heart illustrating an intravascular blood pump system having a "rapid exchange" or "side-rigger" type guide mechanism according to a second broad aspect of the present invention positioned, by way of example, in a trans-valvular configuration to provide left-heart assist.

Referring to FIG. 6, shown is a guidable intra-vascular blood pump system 120 according to a second broad aspect of the present invention. As will be described hereinafter, the intravascular blood pump system 120 differs from the intravascular blood pump system 10 described above only as to the type of guide mechanism employed. In the interest of clarity and consistency, then, like reference numerals will be used to denote like elements and distinctions pointed out where necessary. Moreover, due to the commmonality of principles employed in both intravascular blood pump systems 10, 120, a discussion to the level of detail set forth above is not deemed necessary with regard to the intravascular blood pump system 120. Instead, those aspects in common with the intravascular blood pump 10 are hereby incorporated into the discussion of the intravascular blood pump system 120.

In its most general form, the intravascular blood pump system 120 of this second broad aspect of the present invention comprises the blood pump 12 and cannula 14 arrangement, wherein the cannula 14 is equipped with a "side-rigger" or "rapid exchange" guide mechanism 122. In an important aspect of the present invention, the "rapid exchange" or "side-rigger" guide mechanism 122 includes a guide carriage 124 formed along at least a portion of the cannula 14, and a suitable guide element (such as guide wire 22) dimensioned to pass slidably through a lumen (not shown) extending through the guide carriage 124. The "rapid exchange" guide mechanism 122 thereby provides the ability to selectively guide the blood pump 12 and cannula 14 to a predetermined position in the circulatory system of a patient in the manner described above. Namely, the guide wire 22 may be first introduced into the vascular system of a patient through any suitable access point and guided to a desired location within the circulatory system of the patient, i.e. the left ventricle as shown. The blood pump 12 and cannula 14 may thereafter be advanced along the guide wire 22 and positioned in the transvalvular configuration shown for providing left-heart assist.

Figure 9:
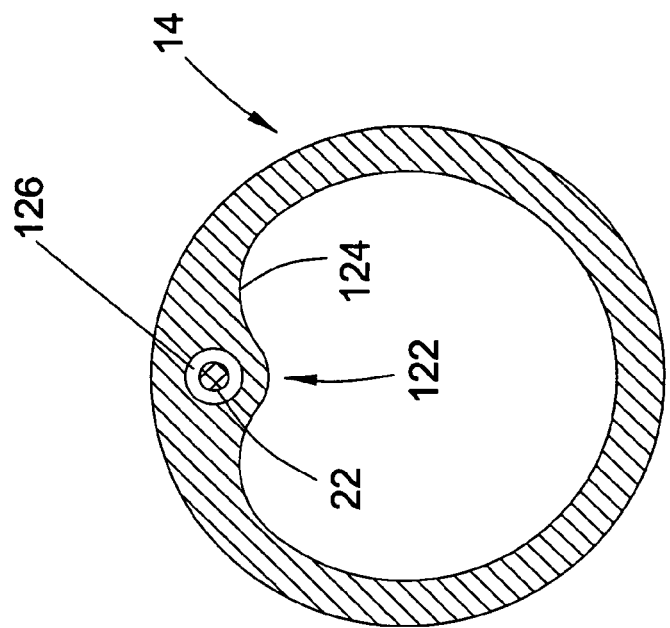
FIG. 9 is a cross-sectional view of the type shown in FIG. 8 illustrating an alternate configuration of the guide mechanism according to the second broad aspect of the present invention.
Figure 8:
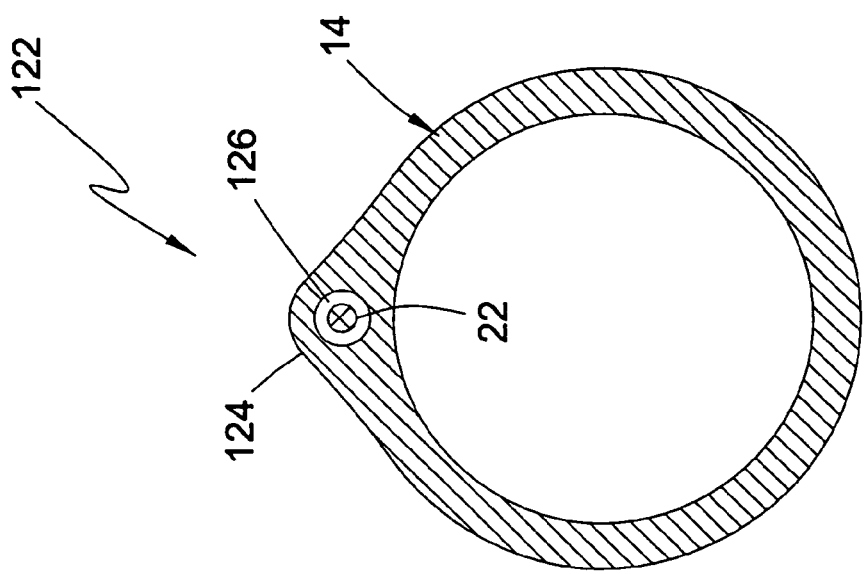
FIG. 8 is a cross-sectional view taken along lines 8-8 of FIG. 7 illustrating the "side-rigger" or "rapid exchange" type guide mechanism according to the second broad aspect of the present invention.

FIGS. 7-9 further illustrate the "side-rigger" or "rapid-exchange" guide mechanism 122 of this second broad aspect of the present invention. In a preferred embodiment, the "side-rigger" guide mechanism 122 includes a lumen 126 formed within the guide carriage 124. The guide carriage 124 is preferably formed as an integral extension of the wall of the cannula 14. FIGS. 7 and 8 comport with the embodiment shown in FIG. 6, namely illustrating the guide carriage 124 formed along the exterior surface of the cannula 14. FIG. 9 illustrates an alternate embodiment wherein the guide carriage 124 may be formed along the interior surface of the cannula 14. In either case, the guide wire 22 is advanced to a desired location in the vasculature of the patient, after which point the blood pump 12 and cannula 14 can be slidably advanced therealong for delivery to the desired location according to the present invention. The guide wire 22 may thereafter be withdrawn from the patient. If the guide carriage 124 is formed along the exterior surface of the cannula 14 (as shown in FIGS. 7-8), then the cannula 14 should preferably be positioned so that the guide carriage 124 does not extend in a trans-valvular fashion. For example, with reference to FIG. 6, the guide carriage 124 should be positioned wholly within the left ventricle such that the pulsatile blood flow during beating heart procedures will not inadvertently pass through the side lumen 126 and pass through the aortic valve.

The intravascular blood pump system 120 is constructed in virtually the same manner as the intravascular blood pump system 10 shown and described above, with the exception of the location of the respective guide mechanisms 16, 122. More specifically, because the guide mechanism 122 is disposed along the side of the cannula 14, there is no need to form a central lumen extending through the blood pump 12, drive cable assembly 18, purge fluid delivery system 26, and motor coupler 24 as detailed above with regard to the intravascular blood pump system 10. As such, these components need not be specially machined or molded to include such central lumens as was required with the intravascular blood pump system 10 set forth above.

Figure 10:
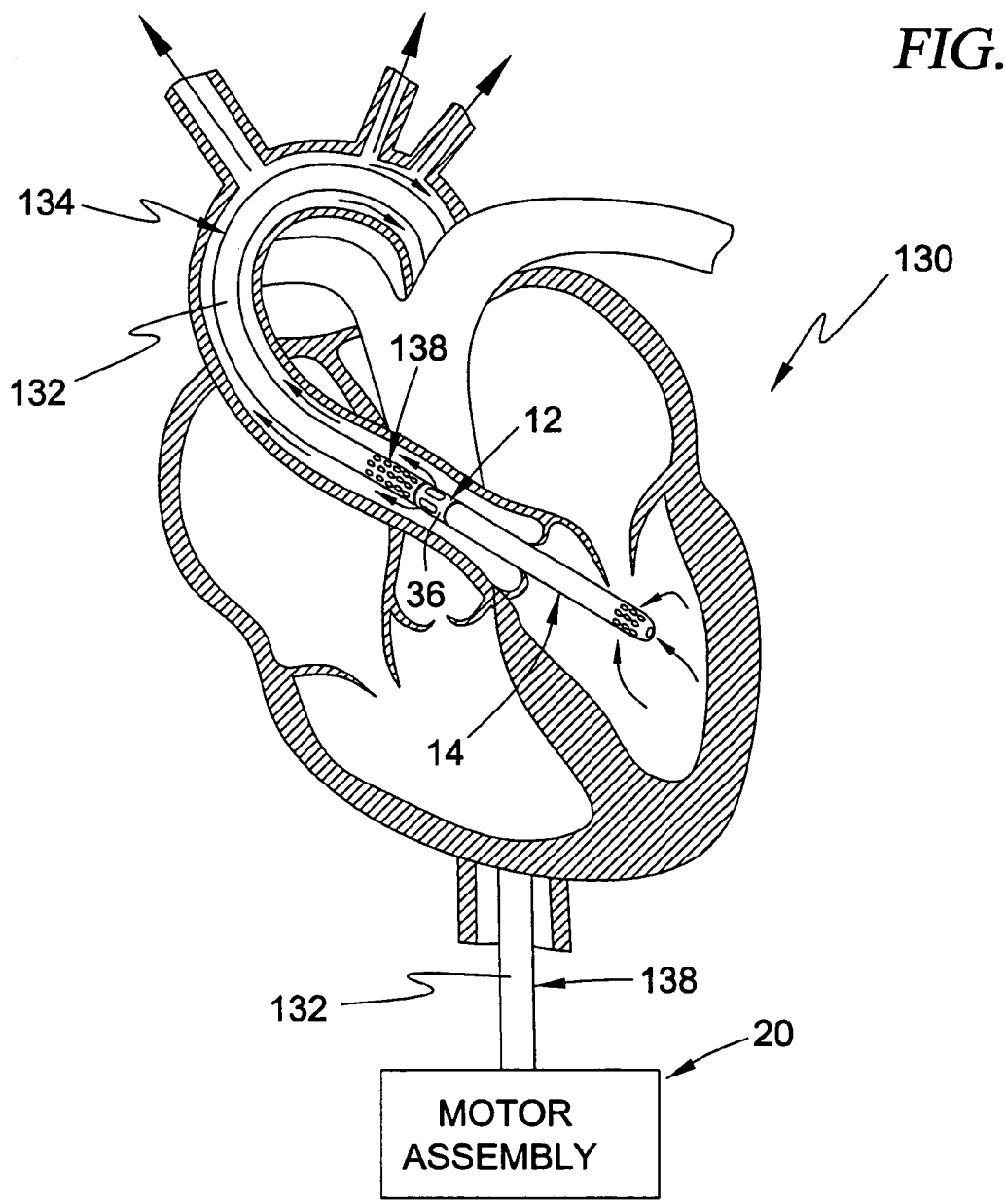
FIG. 10 is a partial sectional view of a human heart illustrating an intravascular blood pump system having a "guide catheter" type guide mechanism according to a third broad aspect of the present invention positioned, by way of example, in a trans-valvular configuration to provide left-heart assist.

Referring to FIG. 10, shown is a guidable intravascular blood pump system 130 according to a third broad aspect of the present invention. Again, due to the commonality between many of the same components and features of the intravascular blood pump systems described above and the intravascular blood pump system 130, like reference numerals will be used to denote like elements and distinctions pointed out where necessary. As will be explained in greater detail below, the intravascular blood pump system 130 employs yet another unique and useful guide mechanism according to the present invention. However, because many of the same components are employed, a discussion to the level of detail set forth above is not deemed necessary with regard to the intravascular blood pump system 130. Instead, those aspects in common with the intravascular blood pumps described above are hereby incorporated into the discussion of the intravascular blood pump system 130.

In its most general form, the intravascular blood pump system 130 of this third broad aspect of the present invention comprises the blood pump 12 and cannula 14 arrangement, wherein a "guide catheter" 132 is provided as the guide mechanism for positioning the pump 12 and cannula 14 at a desired location within the circulatory system of the patient. More specifically, with brief reference to FIG. 12, the intravascular blood pump system 130 is formed in two separate assemblies according to the present invention: a conduit assembly 134 and pump assembly 136. In its most basic form, the conduit assembly 134 comprises the guide catheter 132 and cannula 14 coupled to the. Rotor shroud 35. The pump assembly 136 is constructed such that the pump body 34 and rotor 44 can be disengaged from the rotor shroud 36 and removed entirely from the conduit assembly 134. Referring again to FIG. 10, this dual construction forms a significant feature of the present invention because it provides the ability to form the blood pump 12 at a desired location in a patient using two separate and distinct steps. The first step involves positioning the conduit assembly 134 (with the pump assembly 136 removed) within a patient such that the shroud 36 and cannula 14 are each disposed in a desired location, such as a trans-valvular configuration for cardiac assist procedures. In an important aspect, the task of positioning the conduit assembly 134 within the patient may be advantageously facilitated through the use of any number of well known guidance mechanisms, including but not limited to guide wires, balloon catheters, imaging wires, guide catheters, and/or techniques involving ultra-sound or flouroscopy. The second step in providing the intravascular blood pump system 130 of the present invention involves advancing the pump assembly 136 through the conduit assembly 134 such that the rotor 44 docks within the shroud 36 to form the pump 12 at the desired location.

By way of clarification, the term "cannula" is used to denote cannula 14 because it serves a primary purpose of transporting fluid into the blood pump 12, whereas the term "catheter" is used to denote the catheter 132 because it serves a primary purpose of guiding or directing devices or components (i.e. the pump assembly 136) to a desired location within the body. It is to be readily understood, however, that these terms are only used for convenience and in a general fashion such that the cannula 14 may serve certain guiding functions and the catheter 132 may serve certain fluid transportation functions without departing from the scope of the present invention. For example, the cannula 14 may be equipped with dedicated lumens to receive various guide mechanisms (such as guide wires, balloon catheters, selectively deformable elements such as Nitonol, etc). In similar fashion, the guide catheter 132 may be used to transport fluid to and/or from the patient, such as by providing apertures 138 along predetermined regions of the catheter 132.

Figure 11:
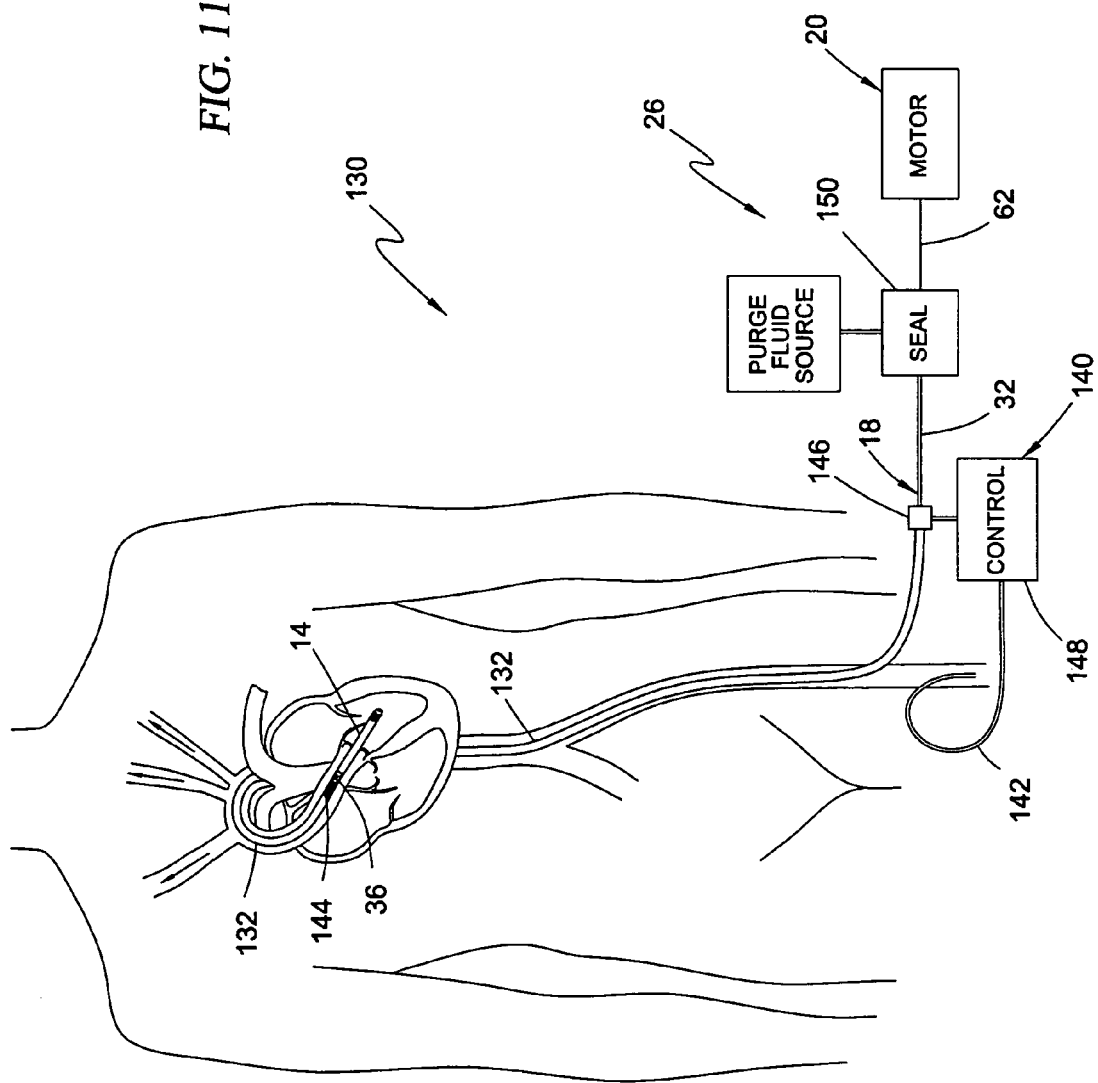
FIG. 11 is a schematic view of a human being illustrating the intravascular blood pump system of the type shown in FIG. 10 inserted through the femoral artery and including an optional perfusion assembly for perfusing the vasculature downstream from the incision site where guide catheter enters the femoral artery.

FIG. 11 demonstrates a significant feature of the present invention involving the use of the guide catheter 132 to transport fluid to and/or from the patient. An optional perfusion assembly 140 is provided as part of the intravascular blood pump system 130 of the present invention. The perfusion assembly 140 includes a conduit 142 in fluid communication with the apertures 138, which in this case are formed near the distal region of the guide catheter 132 a short distance downstream from the blood pump 12. In use, blood will pass along the exterior of the guide catheter 132 for distribution throughout the body, as well as within the interior of the guide catheter 132 after passing into the apertures 138. The perfusion assembly 140 may then be employed to selectively reroute blood from within the guide catheter 132 to a point within the patient's vasculature downstream from the point where the guide catheter 132 enters the body. A hemostasis valve assembly 146 of the perfusion assembly 140 permits the drive cable assembly 18 to pass through to the purge fluid delivery system 26 while preventing blood flow other than into the perfusion assembly 140. A seal assembly 150 of the purge fluid delivery system 26 permits the drive cable 62 to pass through to the motor 20 while preventing the flow of purge fluid other than into and from the purge fluid delivery system 26. The perfusion assembly 140 includes a control mechanism 148 for selectively controlling the distribution of perfusion blood flow from the perfusion assembly 140 into the patient. This control mechanism 148 may be automatic based on certain feedback criteria or manually operated.

Figure 12:
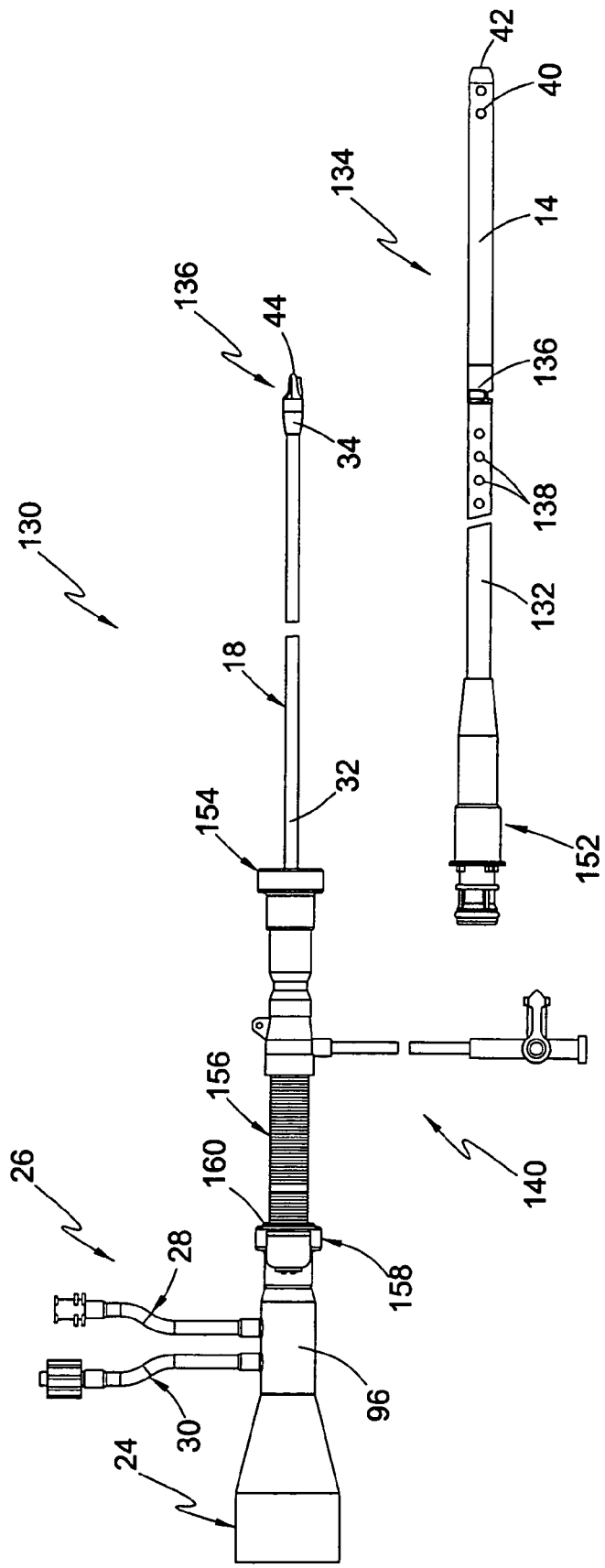
FIG. 12 is a side view of the intravascular blood pump system shown in FIGS. 10-1*i* illustrating the separable nature of a pump assembly and a conduit assembly which collectively form the intravascular blood pump system according to the third broad aspect of the present invention.

FIGS. 12-17 illustrate an exemplary construction of the intravascular blood pump system 130 according to the third broad aspect of the present invention. As shown in FIG. 12, the conduit assembly 134 may be selectively disengaged so as to remove the pump assembly 136 therefrom. According to the present invention, the conduit assembly 134 may be introduced (without the pump assembly 136) into the circulatory system of a patient and selectively guided such that the rotor shroud 36 and cannula 14 are positioned at a desired location. The pump assembly 136 can thereafter be selectively introduced into the conduit assembly 134. A challenge in such a "back-loading" arrangement is ensuring that the pump assembly 136 docks appropriately within the rotor shroud 36 and is maintained in proper engagement during operation of the resulting pump 12.

Figure 14:
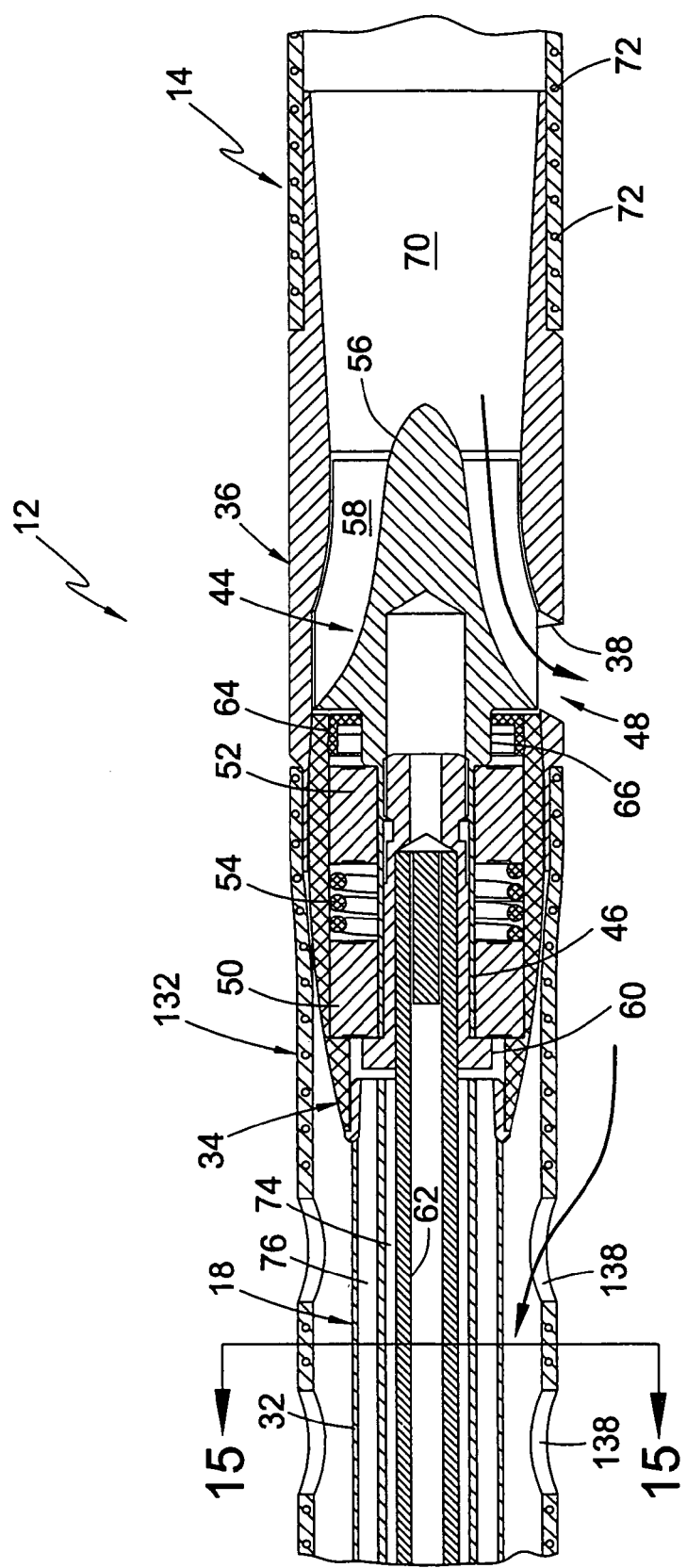
FIG. 14 is a cross-sectional view illustrating an exemplary construction of the blood pump, drive cable assembly, cannula, and guide catheter of the intravascular blood pump system shown in FIG. 13.
Figure 15:
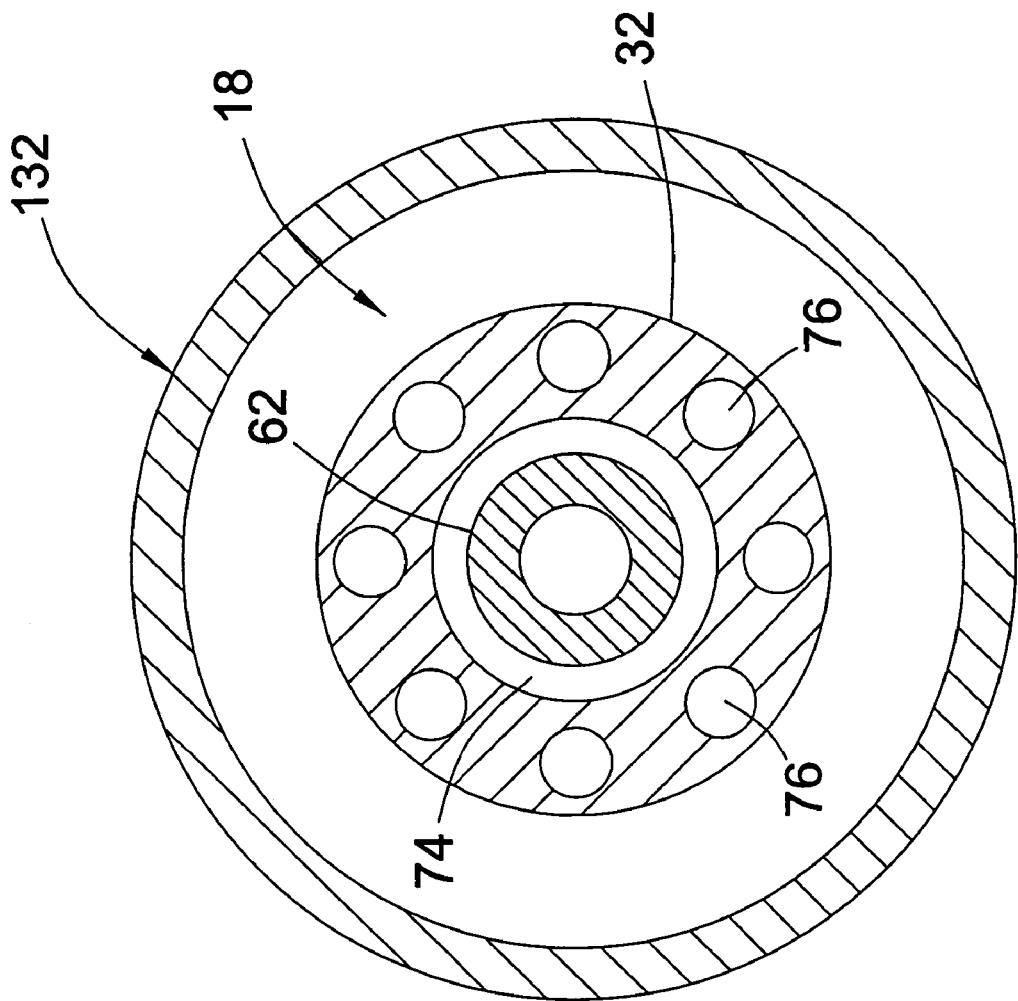
FIG. 15 is a cross-sectional view taken along lines 15-15 of FIG. 14 illustrating an exemplary construction of the drive cable assembly and guide catheter according to the third broad aspect of the present invention.
Figure 16:
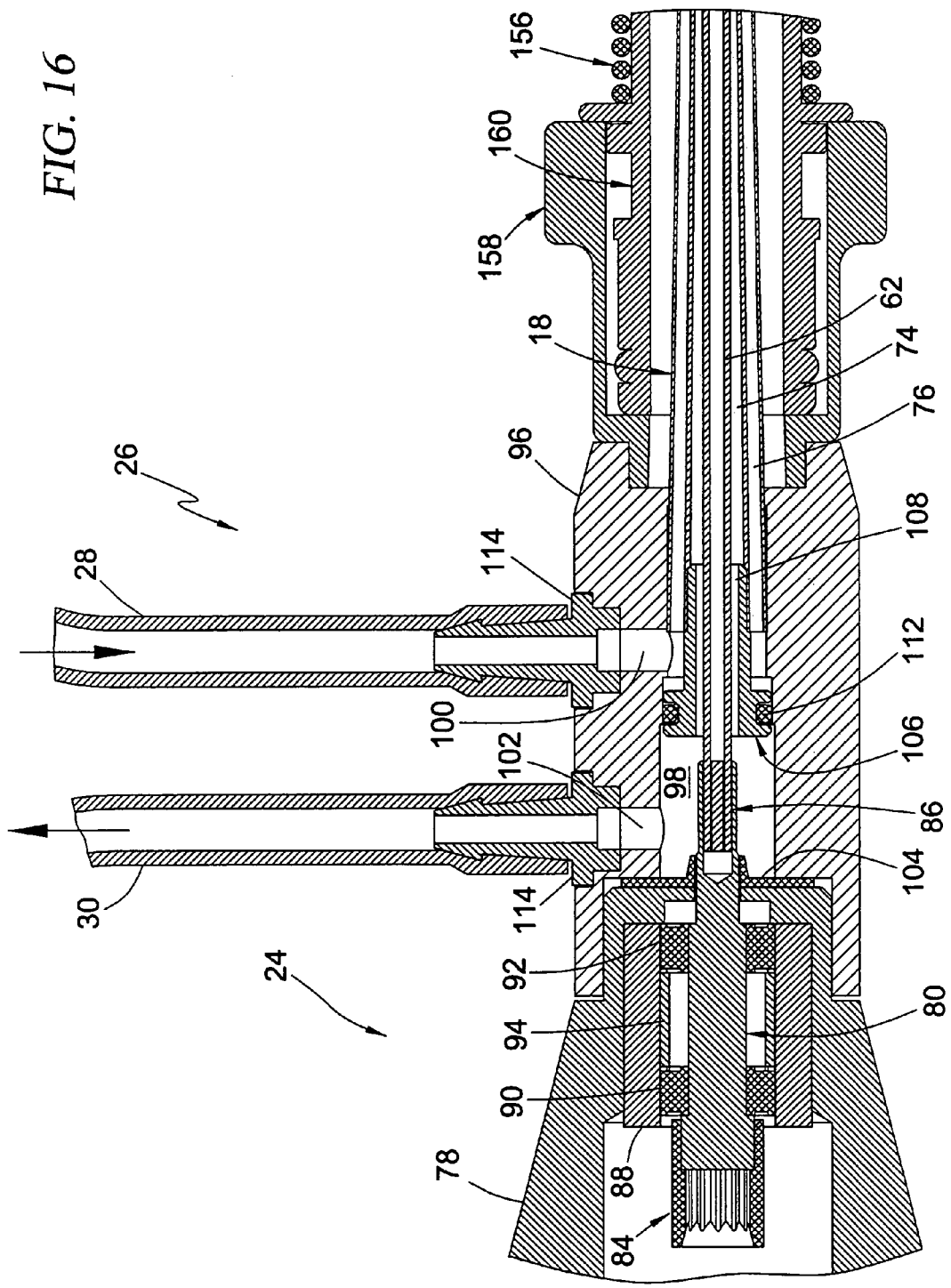
FIG. 16 is a cross-sectional view illustrating an exemplary construction of the motor coupler, purge fluid delivery system, and a proximal portion of the guide catheter biasing assembly according to the third broad aspect of the present invention.

An exemplary docking arrangement will now be described with reference to FIG. 14. In a preferred embodiment, the rotor 44 may be properly and accurately docked within the shroud 36 by forming angled mating surfaces on corresponding portions of the shroud 36 and pump body 34. More specifically, an angled mating surface may be formed on the interior surface of the rotor shroud 36 along that portion extending proximally from the flow aperture 38. A corresponding angled mating surface may be provided along the exterior surface of the pump body 34 along a distal portion thereof. The mating surfaces shown in FIG. 14 may preferably be formed in the range from about 2 degrees to 10 degrees, and more preferably formed in the range from about 3 degrees to 6 degrees. Mating angles within these ranges are adequate to guide the distal end of the pump body 34 to a point generally flush with the proximal edge of the flow aperture 38 as shown in FIG. 14. In this fashion, the pump assembly 136 and the rotor shroud 36 combine to form the blood pump 12. More importantly, this docking is carried out such that the rotor 44 and rotor blades 58 are maintained in proper position for efficient and safe pump operation.

An exemplary biasing scheme for maintaining the pump assembly 136 in this docked relationship will now be described with reference to FIGS. 12-13 and 16-17. The conduit assembly 134 is preferably equipped with a male quick-connect coupling 152 capable of engaging with a female quick-connect coupling 154 forming part of the perfusion assembly 140 of the present invention. A bias spring 156 is provided in between the perfusion assembly 140 and the housing 96 of the purge fluid delivery system 26. The bias spring 156 is preferably dimensioned so as to be in tension when the male quick-connect 152 is engaged within the female quick-connect 154 as part of the docking process of the present invention. As such, the bias spring 156 serves to maintain the pump assembly 136 in the docked position within the rotor shroud 36. The bias spring 156 may be coupled to the housing 96 of the purge fluid delivery system 26 in any number of suitable fashions. One such coupling arrangement may comprise a female quick-connect coupling 158 attached to the housing 96 and a male quick-connect coupling 160 attached to the bias spring 156.

Figure 13:
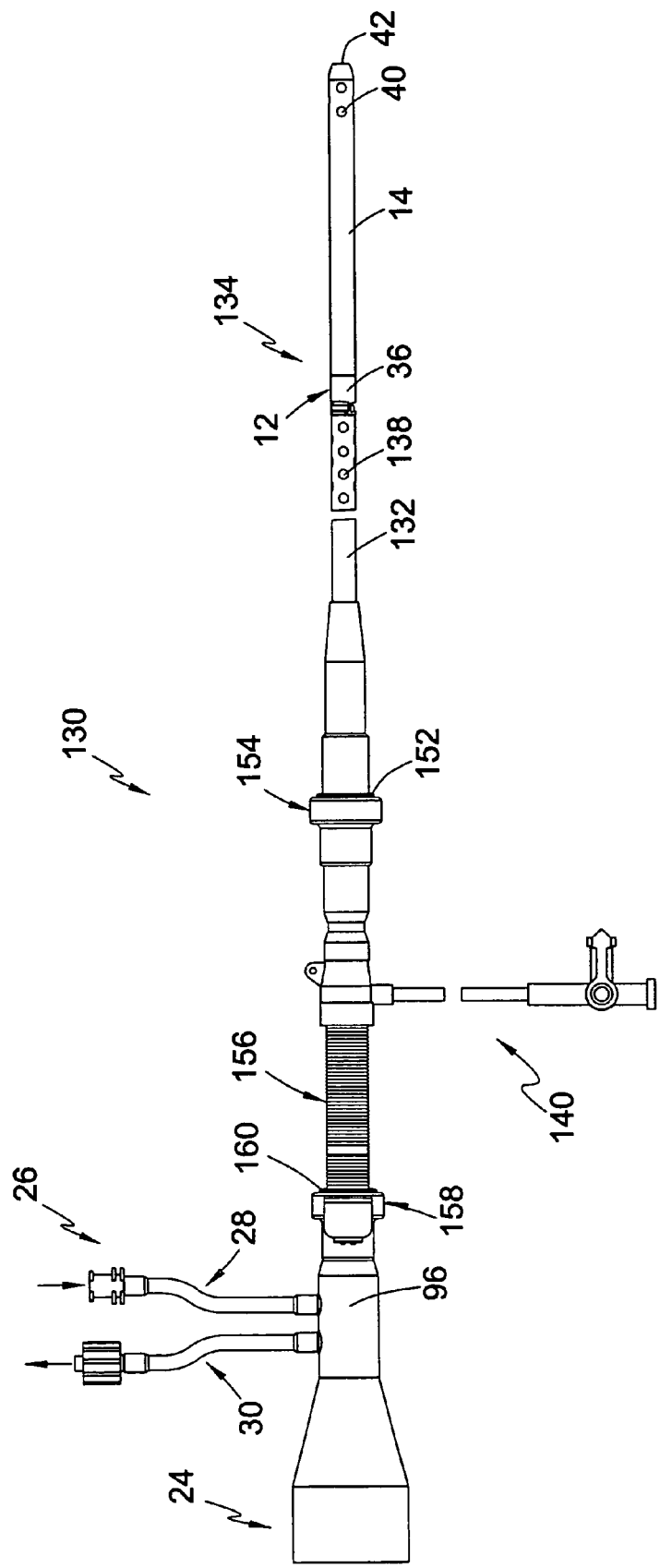
FIG. 13 is a side view illustrating the intravascular blood pump system shown in FIG. 12 with the pump assembly docked into the conduit assembly according to the third broad aspect of the present invention.
Figure 17:
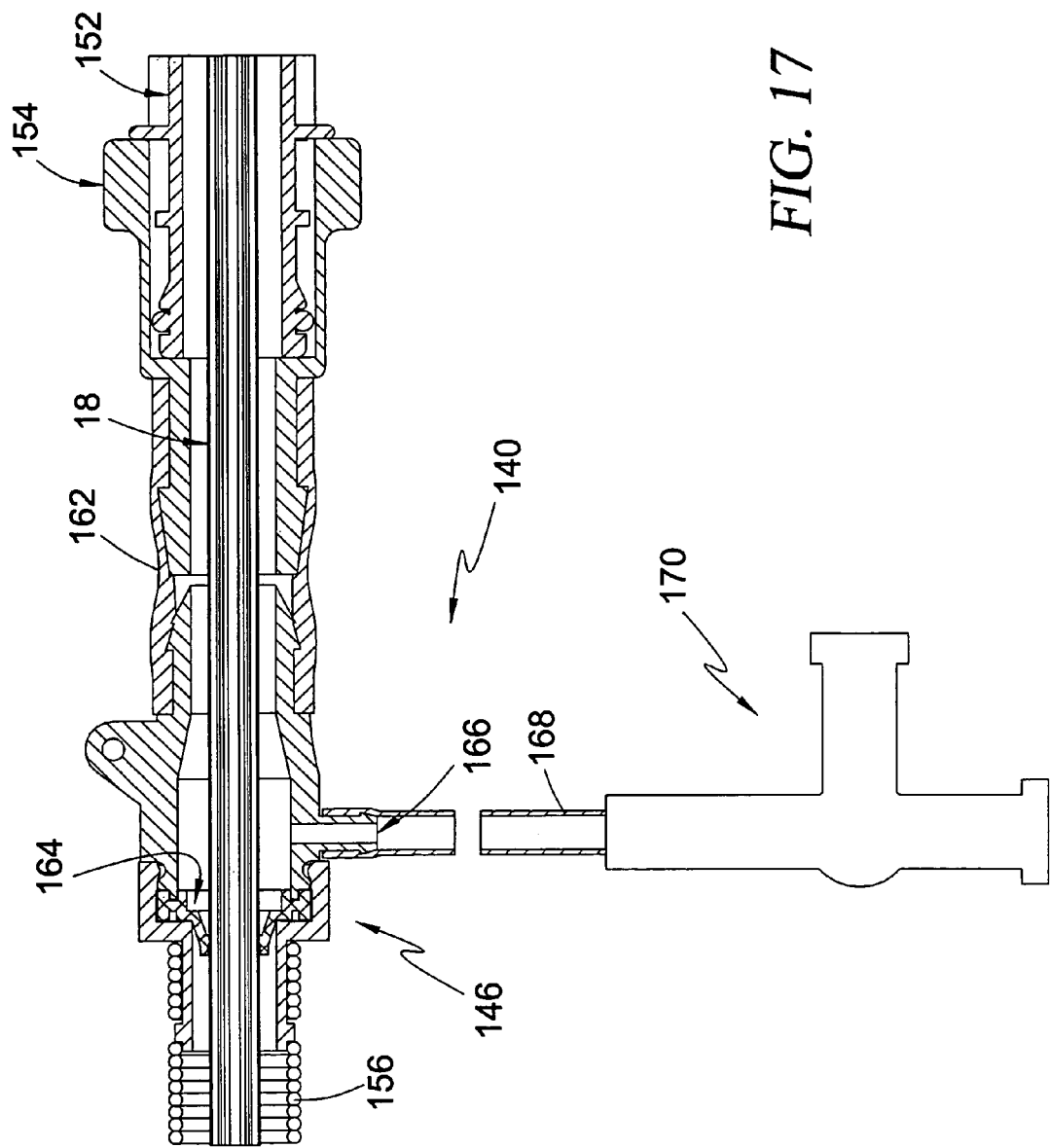
FIG. 17 is a cross-sectional view illustrating an exemplary construction of the perfusion assembly and a distal portion of the guide catheter biasing assembly according to the third broad aspect of the present invention.

An exemplary embodiment of the perfusion assembly 140 is shown with reference to FIGS. 12-13 and 17. The perfusion assembly 140 shown includes the hemostasis valve 146 coupled to the female quick-connect coupling 154. A length of tubing 162 extends between the opposing barb connectors of the hemostasis valve 146 and the female quick-connect coupling 154. A continuous lumen is formed extending through the interior of the male quick-connect coupling 152, the female-quick-connect coupling 154, the tubing 162, and the hemostasis valve 146. The drive cable assembly 18 extends through this continuous lumen and exits through a Touehy-Borst hemostasis seal 164 which prevents the migration of blood out of the proximal end of the perfusion assembly 140. A side-port 166 is disposed in fluid communication with the central lumen of the perfusion assembly 140. In one embodiment, this side-port 166 may be equipped with a conduit 168 having a stop-cock 170 to selectively control the distribution of blood through a perfusion conduit (i.e. conduit 142 of FIG. 11) coupled to the stop-cock 170. It will be appreciated that this type of manual control system for selectively perfusing the patient may be replaced with control circuitry for automatically controlling the rate of perfusion. Such automatic perfusion may be based on control algorithms based on contemporaneous feedback or pre-programmed thresholds.

The foregoing discussion details a host of inventive aspects forming part of the present invention. It will be appreciated by those skilled in the art that changes could be made to the embodiments described above without departing from the broad inventive concepts thereof. The following evidences, by way of example only, various additional aspects forming part of the present invention.

Figure 18:
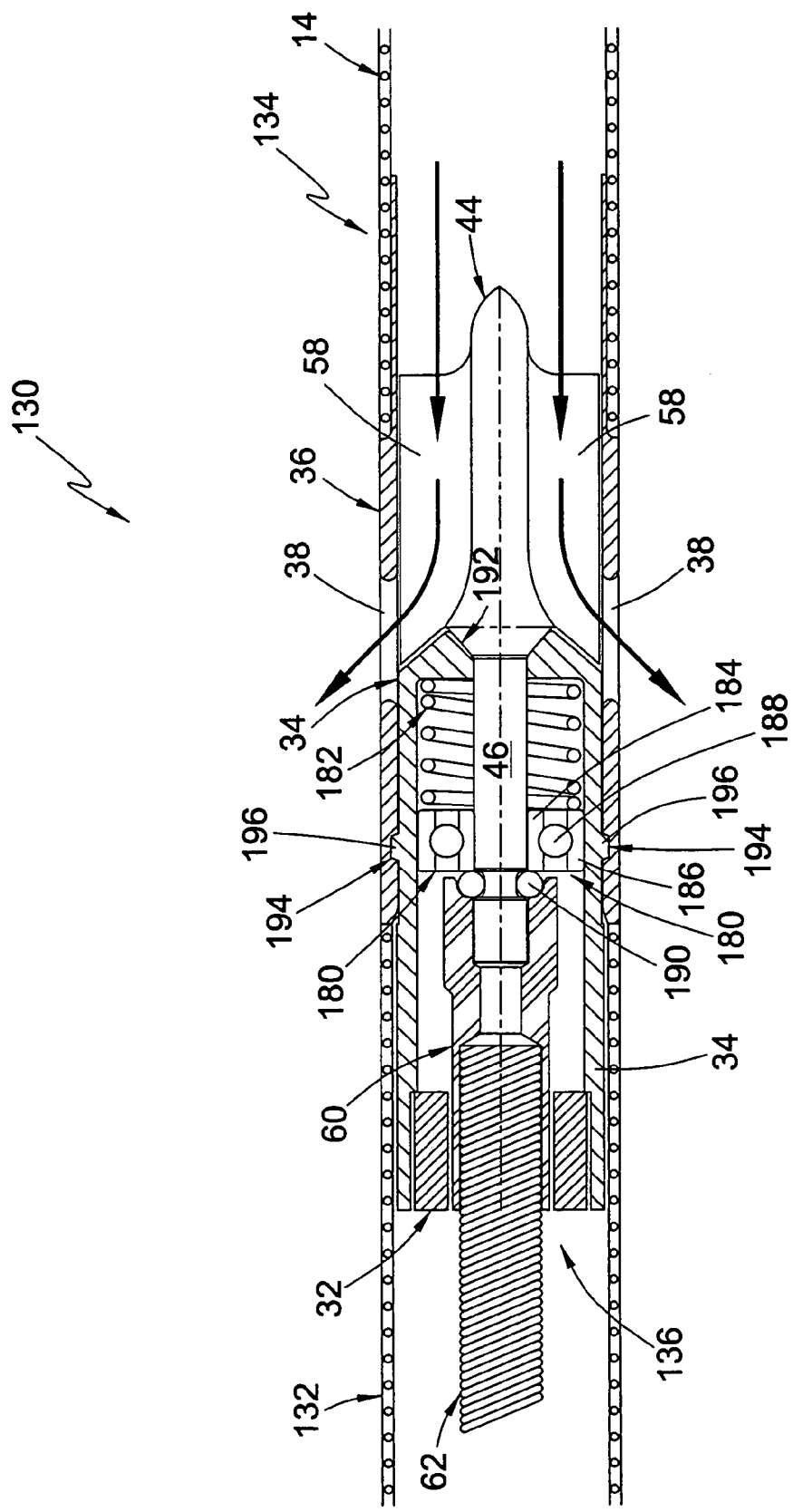
FIG. 18 is a cross-sectional view of an intravascular blood pump system of the type shown in FIGS. 12-13 having an alternate configuration for docking the rotor within the shroud according to the principles of the present invention.

FIG. 18 illustrates an alternate configuration of the intravascular blood pump system 130 of the third broad aspect of the present invention having an alternate bearing assembly, purge fluid delivery, and docking scheme. The bearing assembly includes a seal spring 182 and a bearing assembly 180. The bearing assembly 180 includes an inner race 184, an outer race 186, and a plurality of balls 188 which enable the inner race 184 to rotate along with the rotor shaft 46 while the outer race 186 remains in a static and fixed position relative to an inner surface of the pump body 34. An O-ring 190 is disposed within a groove formed in the rotor shaft 46 so as to maintain the bearing assembly 180 against the seal spring 182. The O-ring 190 is further secured within the groove in the rotor shaft 46 via a contoured lip portion extending from the distal end of the cable adapter 60. The proximal end of the cable adapter 60 flushly engages the drive cable 62.

The purge fluid delivery system of the embodiment shown in FIG. 18 provides for a one way delivery of purge fluid to the blood pump 12. That is, pressurized fluid (namely, fluid pressurized to some level elevated above the blood pressure in the surrounding vessel) is injected in between the drive cable 62 and the interior of the protective sheath 32 during operation. This serves to reduce any-frictional heating that exists between the drive cable 62 and sheath 32. The pressurized fluid also flows through the interior of the pump 12 such that, if the seal at 192 is broken, the pressurized fluid will flow past the open seal 192 and onward through the blood flow ports 38 formed in the shroud 36. This serves to keep blood from entering the pump 12 in an effort to avoid clotting and/or damaging the pump 12.

The pump assembly 136 may be docked within the conduit assembly 134 in any number of different fashions without departing from the scope of the present invention. That is to say, the docking scheme shown in FIG. 18 is set forth by way of example only and is not to be deemed limiting or restrictive as to numerous ways to temporarily engage or "dock" the pump assembly 136 within the conduit assembly 134. The only requirement is that the pump assembly 136 and conduit assembly 134 dock such that the rotor 44 is disposed within the shroud 36 to provide the desired axial flow through the cannula 14 and out the shroud 36. The exemplary docking scheme involves forming an annular engagement groove 194 along the interior of the shroud 36, and forming a complementary annular ridge 196 along the exterior surface of the pump body 34. During insertion, the pump assembly 136 will be advanced into the conduit assembly 134 until the annular ridge 196 on the pump body 34 engages within the groove 194 formed in the shroud 36. This docking scheme is generally advantageous in that the engagement action between the annular ridge 196 and groove 194 will provide tactile feedback to the physician during the process of inserting the pump assembly 136 into the conduit assembly 134 such that the physician will be able to determine when the docking has been completed.

As will be appreciated by those skilled in the art, the location of the annular ridge 196 and engagement groove 194 may be varied such that they are disposed closer or farther away from the flow apertures 38. It may be advantageous to form these docking structures close to the flow apertures 38 in an effort to thwart the ingress of blood into the junction extending between the interior of the shroud 36 and the exterior surface of the pump body 34. It is also contemplated to employ selectively inflatable structures, such as balloons, in an effort to temporarily engage or dock the pump assembly 136 within the conduit assembly 134. In this regard, one or more lumens may be formed within the pump body 34 extending from the interior of the pump body 34 in fluid communication with a balloon disposed along the exterior surface of the pump body 34. The pressurized fluid flowing within the interior of the pump body 34 may then be used to inflate the balloon, which will then engage within an annular groove in the shroud 36, such as at 194. Of course, the engagement structures may also be reversed without departing from the scope of the present invention. For example, the shroud 36 may be equipped with a fluid delivery lumen therein for inflating a balloon disposed on the interior surface of the shroud 36, which may in turn be disposed within an annular engagement groove formed along the exterior surface of the pump body 34.

Figure 19:
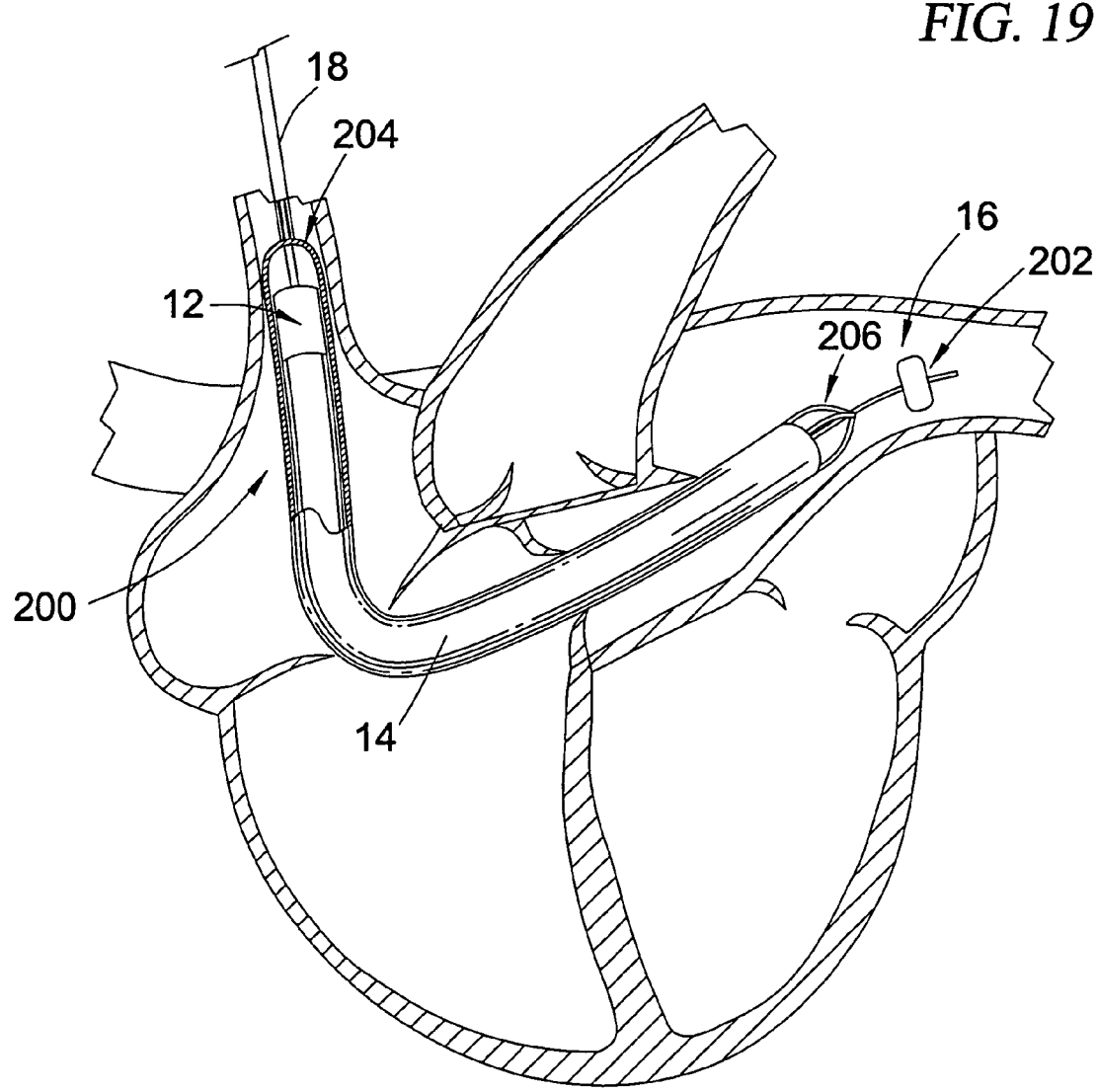
FIG. 19 is a partial sectional view of a human heart illustrating an alternate intravascular blood pump system having an "over-the-wire" type guide mechanism according to the first broad aspect of the present invention positioned, by way of example, in a trans-valvular configuration to provide right-heart assist.

While this invention has been shown in use largely in during left-heart applications it is to be readily appreciated that this does not limit the applications of this invention for use in left heart support only. Rather, the guidable intravascular blood pump of the present invention can be utilized in right-heart support applications and a wide variety of other applications apparent to those skilled in the art. For example, with reference to FIG. 19, shown is an intravascular blood pump 200 (of the type shown and described above with reference to FIGS. 2-5) configured for use in a right-heart support application. In this embodiment, the intravascular blood pump system 200 is equipped, by way of example, with an "over-the-wire" guide mechanism 16 comprising a balloon catheter 202. It is to be readily appreciated that, although shown and described below in terms of an embodiment of the type shown in FIGS. 2-5, the intravascular blood pump systems 120, 130 disclosed herein may also be configured for use in right-heart applications. Such right-heart configurations, and others apparent to those skilled in the art based on the broad principles enumerated in this application, are contemplated as being within the scope of the present invention.

The intravascular blood pump system 200 is shown positioned within the heart, such as may be advantageous to provide right heart support during beating heart surgery. To position the guidable intravascular blood pump system 200 in the right heart according to the present invention, a suitable guide element (such as balloon catheter 202) is first advanced to a desired location within the heart via the "sail" action of an inflated balloon. After the balloon catheter 202 is located in the desired position (such as in the pulmonary artery as shown), the intravascular blood pump system 200 according to the present invention may be advanced over the balloon catheter 202 and guided into a desired arrangement. For right heart support, this would involve advanced into the pump 12 and cannula 14 overt the balloon catheter 202 until the fluid inlet 204 is disposed within the vena cava (or right atrium) and the fluid outlet 206 is positioned within the pulmonary artery. The pump 12 may then be selectively (i.e. automatically or on-demand) controlled to transport blood from the vena cava (or right atrium) in a trans-valvular fashion through the tricuspid valve, the right ventricle, and the pulmonary valve for deposit within the pulmonary artery. Providing right-heart support during beating heart surgery advantageously overcomes conditions where cardiac output may become compromised during beating heart surgery, such as when the heart is lifted to gain access to posterior vessels, thereby avoiding the need for cardiopulmonary bypass.

It is also contemplated as part of the present invention that the guidable intravascular blood pump systems can be introduced into the patient's vasculature to achieve the intravascular access into the right or left heart through any number of access points, including but not limited to the internal jugular vein, the brachiocephalic vein, carotid artery, axillary artery, femoral vein, femoral artery, and subclavian artery. The intravascular blood pump systems of the present invention may also be introduced via direct introduction, such as into the aorta, the atria, and the ventricles. As is well known in the art, such intravascular access may be achieved percutaneously through the use of the Seldinger technique or directly through the use of minimally invasive access techniques.

Those skilled in the art will also appreciate that, although shown and described above in terms of "axial flow," the present invention is not limited to the axial flow type intravascular blood pumps. Rather, the intravascular blood pumps 12 may comprise any number of suitable types of intravascular blood pumps, including but not limited to so-called "mixed flow" intravascular blood pumps, without departing from the scope of the present invention.

With regard to the embodiments shown in FIGS. 10-17, it is furthermore contemplated that the guide catheter 132 may be separable from the conduit assembly 134 after the pump assembly 136 is docked within the shroud 36 to form the pump 12 at the desired location within the circulatory system of the patient. This may be accomplished by providing the guide catheter 132 in a detachable fashion via any number of suitable arrangements. By removing the guide catheter 132 after the pump 12 assembled, wound management of the access point into the patient's vasculature may be improved. This is due, in part, to the substantial reduction in size of the device extending into the patient (i.e. the drive cable assembly 18 as opposed to the larger diameter guide catheter 132).

It is also contemplated to incorporate various pressure sensing and/or guidability features into at least one of the cannula, 14 and pump 12. Such features may include, but are not necessarily limited to, those shown and described in commonly-owned and co-pending U.S. patent application Ser. No. 09/280,988 (filed Mar. 30, 1999) entitled "Steerable Cannula," and U.S. patent application Ser. No. 09/280,970 (filed Mar. 30, 1999) entitled "Pressure Sensing Cannula," the disclosures of which are hereby expressly incorporated by reference as if set forth herein in their entirety. These pressure sensing features may include, but are not necessarily limited to, the use of fluid-filled lumens, piezo-electric pressure sensing elements, strain gauges, and analysis of the torque/current relationship (based on the dynamic pressure differential between the inlet and outlet of the pump). The guidability features may include, but are not necessarily limited to, the use of side lumens and deformable materials (i.e. Nitonol).

Various pump and cannula arrangements have been described and shown above for providing right and/or left heart support wherein blood is deliberately re-routed through and past the right and/or left ventricle in an effort to reduce the volume of blood to be pumped by the particular ventricle. While "unloading" the ventricles in this fashion is preferred in certain instances, it is to be readily understood that the pump and cannula arrangements described herein may also be employed to "preload" the ventricles. Ventricular preloading may be accomplished by positioning the outflow cannula from the pump into a given ventricle such that the pump may be employed to fill or preload the ventricle with blood. This may be particularly useful with the right ventricle. On occasion, the right ventricle is not supplied with sufficient levels of blood from the right atrium such that, upon contraction, the right ventricle delivers an insufficient quantity of blood to the pulmonary artery. This may result when the right ventricle and/or right atrium are in a stressed or distorted condition during surgery. Preloading overcomes this problem by actively supplying blood into the right ventricle, thereby facilitating the delivery of blood into the pulmonary artery. The same technique can be used to preload the left ventricle and thus facilitate the delivery of blood from the left ventricle into the aorta.

What is claimed is:

1. An intravascular blood pump system, comprising:
an intravascular blood pump having a cannula releasably coupled thereto, said intravascular blood pump including a rotor, a shroud for receiving said rotor, a biasing member biasing said rotor towards a docking position in which said rotor is received in said shroud, and a drive cable securedly coupled to said rotor for driving said rotor within said shroud;
wherein said system comprises a pump assembly separable from a conduit assembly, said conduit assembly comprising said cannula and said, shroud, and said pump assembly comprising said rotor, said biasing member and said drive cable; and
a central lumen extending through said shroud and said cannula for receiving a guide mechanism therethrough.

2. The system of claim 1, wherein said central lumen further extends through said rotor and said drive cable.

3. The system of claim 2, further comprising a guide mechanism extending though said central lumen.

4. The system of claim 1, further comprising an impeller having a hub, said hub having a central lumen therethrough and a gasket or seal at a distal end portion of said hub, said gasket or seal configured to seal said central lumen through said hub and prevent ingress of blood into an interior of said hub during operation of said blood pump system.

5. The system of claim 1, further comprising a quick-connect coupling provided on said conduit assembly, and a mating quick-connect coupling provided on said pump assembly, said quick-connect coupling and said mating quick-connect coupling being mateable to maintain said rotor and said shroud in said docking position, and releasable to remove and separate said rotor and said shroud from said docking position.

6. An intravascular blood pump system, comprising:
   a pump assembly provided independent of and separable from a conduit assembly;
   said conduit assembly comprising a cannula coupled to a shroud;
   said pump assembly comprising a rotor and a drive cable coupled to said rotor and configured to drive said rotor; and
   wherein said pump assembly is dockable with said conduit assembly such that said rotor is receivable within said shroud and removable from said shroud by releasable docking thereof.

7. The system of claim 6, wherein said conduit assembly further comprising a guide mechanism extending proximally of said shroud.

8. The system of claim 7, wherein said guide mechanism comprises a guide catheter.

9. A method of installing a blood pump assembly within a location in a patient, said method comprising:
   positioning a conduit assembly within the patient, such that a shroud connected to a cannula of said conduit assembly is positioned in a desired location and wherein a pump assembly is not connected to said conduit assembly during said positioning;
   introducing a pump assembly into the patient and advancing the pump assembly to the position of the conduit assembly; and
   docking the pump assembly with the conduit assembly such that a rotor of the pump assembly is received within the shroud.

10. The method of claim 9, wherein said conduit assembly is advanced intravascularly to perform said positioning.

11. The method of claim 9, wherein said conduit assembly includes a guide catheter extending proximally of said shroud, and said advancing the pump assembly comprises advancing at least a distal end portion of said pump assembly through said guide catheter.

* * * * *